(12) United States Patent
Miyamoto et al.

(10) Patent No.: US 8,354,392 B2
(45) Date of Patent: Jan. 15, 2013

(54) DRUG-INTRODUCED PHOTO-CROSSLINKED HYALURONIC ACID DERIVED GEL

(75) Inventors: Kenji Miyamoto, Higashiyamato (JP); Yousuke Yasuda, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 646 days.

(21) Appl. No.: 11/994,981

(22) PCT Filed: Jul. 5, 2006

(86) PCT No.: PCT/JP2006/313412
§ 371 (c)(1), (2), (4) Date: Jan. 7, 2008

(87) PCT Pub. No.: WO2007/004675
PCT Pub. Date: Jan. 11, 2007

(65) Prior Publication Data
US 2009/0118348 A1 May 7, 2009

(30) Foreign Application Priority Data

Jul. 6, 2005 (JP) ................................. 2005-198176

(51) Int. Cl.
*A61K 31/728* (2006.01)
*C07H 5/06* (2006.01)

(52) U.S. Cl. ......................................... 514/54; 536/55.1
(58) Field of Classification Search .................. None
See application file for complete search history.

(56) References Cited

U.S. PATENT DOCUMENTS

| | | | |
|---|---|---|---|
| 5,770,229 A | 6/1998 | Tanihara et al. | |
| 6,031,017 A | 2/2000 | Waki et al. | |
| 6,602,859 B2 | 8/2003 | Miyamoto et al. | |
| 2002/0143121 A1 | 10/2002 | Miyamoto et al. | |
| 2007/0197465 A1* | 8/2007 | Ikeya et al. | 514/54 |
| 2008/0221062 A1* | 9/2008 | Miyamoto et al. | 514/54 |
| 2008/0292703 A1* | 11/2008 | Renier et al. | 424/484 |

FOREIGN PATENT DOCUMENTS

| | | |
|---|---|---|
| EP | 0 554 898 A2 | 8/1993 |
| EP | 713859 | 5/1996 |
| EP | 1 082 963 A1 | 3/2001 |
| JP | 06-073102 | 3/1994 |
| JP | 09-188705 | 7/1997 |
| JP | 11-512778 | 11/1999 |
| JP | 2001-329002 | 11/2001 |
| JP | 3 107488 | 2/2005 |
| WO | WO 89/10941 | 11/1989 |
| WO | WO 97-46261 | 12/1997 |
| WO | WO99/59603 | 11/1999 |
| WO | WO 99/59603 | 11/1999 |
| WO | WO 00/16818 A1 | 3/2000 |
| WO | WO 03/076475 A1 | 9/2003 |
| WO | WO 2004/035629 | 4/2004 |
| WO | WO2005/066214 | 7/2005 |
| WO | WO 2007/126154 A1 | 11/2007 |

OTHER PUBLICATIONS

Reicin et al., "Comparison of Cardiovascular Thrombotic Events in Patients With Osteoarthritis Treated With Rofecoxib Versus Nonselective Nonsteroidal Antiinflammatory Drugs (Ibuprofen, Diclofenac, and Nabumetone)" The American Journal of Cardiology (Jan. 15, 2002) vol. 89, pp. 204-209.*
Pouyani Tara et al.: "Functionalized Derivatives of Hyaluronic Acid Oligosaccharides: Drug Carriers and Novel Biomaterials" Bioconjugate Chemistry, vol. 5, No. 4 1994, pp. 339-347.
Supplemental European Search report related to 06780788.3-1216 1905456.

* cited by examiner

*Primary Examiner* — Eric S Olson
(74) *Attorney, Agent, or Firm* — Husch Blackwell LLP

(57) ABSTRACT

A drug-introduced photo-crosslinked hyaluronic acid derived gel which is a photo-crosslinked hyaluronic acid gel into which a drug is introduced through a covalent bond, and has characteristics that are capable of extruding from an injection device. The drug-introduced photo-cross-linked hyaluronic acid derived gel is capable of extruding, for example, by an injection needle of 20 to 25 gauge with a pressure of 0.5 to 5 kg/cm$^2$.

24 Claims, No Drawings

… … …

DRUG-INTRODUCED PHOTO-CROSSLINKED HYALURONIC ACID DERIVED GEL

CROSS REFERENCE

This application is National Stage Entry of International Patent application PCT/JP2006/313412, filed 5 Jul. 2006, which claims priority from Japanese application JP2005-198176, filed on 6 Jul. 2005.

TECHNICAL FIELD

The present invention relates to a drug-introduced photo-crosslinked hyaluronic acid derived gel in which a drug is introduced into a photo-crosslinked hyaluronic acid by a covalent bond. The present invention also relates to a drug-introduced photo-reactive hyaluronic acid derivative into which a drug and photo-reactive groups are introduced.

BACKGROUND ART

If a drug delivery system (hereinafter also referred to as DDS) in which it can be directly administered to a diseased area by an injection device such as an injection syringe, a sufficient amount of a drug can be retained, it has a sustained release property which can release a drug for a long period of time by stopping at diseased area, and it is safe for a living body, can be utilized, it is extremely useful for the treatment of orthopedic surgery diseases such as osteoarthritis (arthrosis deformans), chronic rheumatoid arthritis, etc., and tumor, etc.

Polysaccharides derived from a living body such as hyaluronic acid (hereinafter also referred to as HA) or glycosaminoglycan (hereinafter also referred to as GAG), etc. have high biocompatibility, various DDS utilizing these polysaccharides have been proposed as of today.

For example, it has been tried to use a substance in which a drug is included in a crosslinked material by mixing a drug with crosslinked hyaluronic acid or hydrating the same for a base material of DDS or a sustained release preparation, and has been reported (Patent Literature 1, etc.). In these materials, a crosslinked HA or a cross-linked GAG and a drug form a complex by an ionic action, whereby a power to retain the drug is weak so that there is a defect that the drug is released within a short period of time when it is administered into a living body. Thus, it cannot obtain sufficient effects with regard to the use for sustained release the drug or for the DDS use to transport the drug to the objective diseased portion.

To the contrary, it has been proposed a material in which a drug is bound to the above-mentioned polysaccharides through a covalent bond, there have been proposed as of today an HA derivative in which a drug is bound to a carboxyl group of HA through an ester bond (Patent Literature 2), a polymer gel in which a drug is bound to a crosslinked alginic acid gel, etc. through a spacer and a peptide decomposable group by a covalent bond (Patent Literature 3), an HA derivative in which a drug is bound to an HA derivative such as HA or crosslinked HA, etc. through a spacer by a covalent bond (Patent Literature 4), and the like.

However, in general, it has been well known when a substance having high hydrophobicity such as a drug, etc., is introduced into a high-molecular weight polysaccharide or HA by a covalent bond, a solubility of the product is markedly lowered so that it is insoluble or semi-insoluble. When a larger amount of a drug is introduced, the product tends to be highly insoluble, whereby it becomes impossible to obtain a material having characteristics capable of injecting through an injection syringe, etc. In the above-mentioned Patent Literature 2, with regard to the HA derivative into which a drug has been introduced, it is not on the assumption to maintain hydrophilicity in view of an introduction of a drug and an amount of a carboxyl group(s) of HA to be used for internal esterification. The polymer gel of Patent Literature 3 is a material swelling by an aqueous liquid, so that it is not a material which can be injected by an injection syringe, etc., and the product into which a drug has been introduced is prepared in a form such as a sheet, a film, etc. In Patent Literature 4, there is no description about characteristics of the product into which a drug has been introduced, and in Examples, an degree of substitution of the drug by binding to a carboxyl group(s) which pertain to solubility is set to low.

As mentioned above, it has not been known DDS using HA as a base which satisfies all the conditions that it is capable of directly administering to a local portion by an injecting tool such as an injection syringe, etc., to diseased area such as a joint, internal organs, etc., it can maintain a sufficient amount of the drug, and it has a sustained release property which can release a drug for a long period of time by staying at diseased area.

On the other hand, the present inventors have proposed a photo-crosslinked hyaluronic acid utilizing a photo-crosslinked group as a hyaluronic acid gel having high hydrophilicity (Patent Literature 5).

[Patent Literature 1] JP-3107488 B
[Patent Literature 2] WO 89/10941
[Patent Literature 3] U.S. Pat. No. 5,770,229
[Patent Literature 4] WO 99/59603
[Patent Literature 5] U.S. Pat. No. 6,602,859

DISCLOSURE OF THE INVENTION

Problems to be Solved by the Invention

An object of the present invention is to provide a drug delivery system in which it can be directly administered to diseased area by an injection device such as an injection syringe, a sufficient amount of a drug can be retained at an administered portion or diseased area, it has a sustained release property which can release a drug for a long period of time by staying at an administered portion or diseased area, and it is safe for a living body. Also, another object of the present invention is to provide an intermediate which is useful for the above-mentioned drug delivery system.

Means to Solve the Problems

The present inventors have intensively studied to solve the above-mentioned problems, and as a result, they have found out that a drug-introduced photo-crosslinked hyaluronic acid derived gel can be provided as a DDS satisfying the above-mentioned requirements by introducing a drug into a photo-crosslinked hyaluronic acid which utilizes a photo-crosslinking group, and they have further investigated on various conditions for containing a drug, whereby the present invention has been accomplished.

That is, the present invention relates to the following (1) to (31).

(1) A drug-introduced photo-crosslinked hyaluronic acid derived gel which comprises a photo-crosslinked hyaluronic acid derived gel in which a drug is introduced therein by a covalent bond, and is in a state of capable of extruding by an injection device.

(2) The drug-introduced photo-crosslinked hyaluronic acid derived gel described in (1), wherein "a photo-reactive group" and "a drug" are each bonded to "the hyaluronic acid" by a covalent bond through a spacer.
(3) The drug-introduced photo-crosslinked hyaluronic acid derived gel described in (1) or (2), wherein it is capable of extruding by an injection needle of 20 to 25 gauge with a pressure of 0.5 to 5 kg/cm$^2$.
(4) The drug-introduced photo-crosslinked hyaluronic acid derived gel described in any one of (1) to (3), wherein "a photo-reactive group" comprises a cinnamic acid derivative or an aminocinnamic acid derivative.
(5) The drug-introduced photo-crosslinked hyaluronic acid derived gel described in any one of (1) to (4), wherein "a drug" is a substance having a functional group(s) which is capable of bonding to a carboxyl group or a hydroxyl group.
(6) The drug-introduced photo-crosslinked hyaluronic acid derived gel described in (5), wherein "a spacer" is a residue of a compound having 2 or more functional groups selected from a carboxylic acid, a hydroxyl group and an amino group.
(7) The drug-introduced photo-crosslinked hyaluronic acid derived gel described in any one of (1) to (6), wherein "a drug" is selected from non-steroidal anti-inflammatory drugs, disease-modifying anti-rheumatic drugs, matrix metalloprotease inhibitors, steroid drugs and anti-cancer drugs.
(8) The drug-introduced photo-crosslinked hyaluronic acid derived gel described in (7), wherein "the drug" is non-steroidal anti-inflammatory drugs or disease-modifying anti-rheumatic drugs.
(9) The drug-introduced photo-crosslinked hyaluronic acid derived gel described in any one of (1) to (8), wherein "a photo-reactive group" and "a drug" are bonded to carboxyl groups of the hyaluronic acid, respectively.
(10) The drug-introduced photo-crosslinked hyaluronic acid derived gel described in any one of (1) to (9), wherein "a photo-reactive group" or "a spacer to which a photo-reactive group is bound" is bound to a carboxyl group of the hyaluronic acid through an amide bond.
(11) The drug-introduced photo-crosslinked hyaluronic acid derived gel described in any one of (1) to (10), wherein "the drug" is directly bound to a carboxyl group of the hyaluronic acid through an ester bond or an amide bond.
(12) The drug-introduced photo-crosslinked hyaluronic acid derived gel described in any one of (1) to (10), wherein "the drug" is bound to "a spacer" through an ester bond, and said spacer bound to the drug is bound to a carboxyl group of the hyaluronic acid through an amide bond.
(13) The drug-introduced photo-crosslinked hyaluronic acid derived gel described in any one of (1) to (12), wherein degree of substitution of "a photo-reactive group" and "the drug" in total are 10 to 45 mol % per a molar number of a repeating disaccharide unit of the hyaluronic acid.
(14) The drug-introduced photo-crosslinked hyaluronic acid derived gel described in any one of (1) to (13), wherein it can be obtainable by subjecting to an alkali treatment before photo-crosslinking in preparation steps.
(15) The drug-introduced photo-reactive hyaluronic acid derivative which comprises "a photo-reactive group" and "a drug" both being bound to "hyaluronic acid" through covalent bonds and is soluble in an aqueous medium.
(16) The drug-introduced photo-reactive hyaluronic acid derivative described in (15), wherein "the photo-reactive group" and "the drug" are both bound to "the hyaluronic acid" via a spacer through covalent bonds.
(17) The drug-introduced photo-reactive hyaluronic acid derivative described in (15) or (16), wherein it can be obtainable by subjecting to an alkali treatment in any steps after introduction of the photo-reactive group and/or the drug into the hyaluronic acid in the preparation steps.
(18) A drug-introduced photo-crosslinked hyaluronic acid derived gel which is obtainable by irradiating ultraviolet rays to an aqueous solution of the drug-introduced photo-reactive hyaluronic acid derivative described in any one of (15) to (17).
(19) The drug-introduced photo-crosslinked hyaluronic acid derived gel described in (18), wherein it is obtainable by sterilization after irradiation of ultraviolet rays.
(20) A drug-filled injection device which comprises the drug-introduced photo-crosslinked hyaluronic acid derived gel described in any one of (1) to (11), (18) and (19) being filled in an injection device which is sealed by a gasket.
(21) The filled injection device described in (20), wherein it has been applied to sterilization.
(22) A drug containing the drug-introduced photo-crosslinked hyaluronic acid derived gel described in any one of (1) to (11), (18) and (19).
(23) A preparation for local administration which comprises the drug-introduced photo-crosslinked hyaluronic acid derived gel described in any one of (1) to (11), (18) and (19).
(24) An agent for treating osteoarthritis comprising the drug-introduced photo-crosslinked hyaluronic acid derived gel described in any one of (1) to (11), (18) and (19).
(25) A drug-sustained release preparation having a property of gradually releasing a drug introduced into hyaluronic acid which comprises the drug-introduced photo-crosslinked hyaluronic acid derived gel described in any one of (1) to (11), (18) and (19).
(26) A drug derivative which comprises a spacer having two or more reactive groups selected from a carboxylic acid, a hydroxyl group and amino group being bonded with a drug through a covalent bond.
(27) The drug derivative described in (26), wherein the drug is selected from non-steroidal anti-inflammatory drugs, disease-modifying anti-rheumatic drugs, matrix metalloprotease inhibitors, steroid drugs and anti-cancer drugs.
(28) A process for preparing a drug-introduced photo-crosslinked hyaluronic acid derived gel capable of injecting which comprises bonding "a photo-reactive group" and "a drug" to "the hyaluronic acid" through a spacer or without a spacer by a covalent bond to obtain a drug-introduced photo-reactive hyaluronic acid derivative, and irradiating an ultraviolet ray to an aqueous solution of the derivative.
(29) A process for preparing a drug-introduced photo-crosslinked hyaluronic acid derived gel capable of injecting, which comprises the steps of preparing a solution by dissolving the drug-introduced photo-reactive hyaluronic acid derivative described in any one of (15) to (17) in an aqueous medium, and irradiating ultraviolet rays to the solution.
(30) Use of a drug-introduced photo-crosslinked hyaluronic acid derived gel for a drug sustained release agent which comprises administering the drug-introduced photo-crosslinked hyaluronic acid derived gel described in any one of (1) to (11), (18) and (19) directly to a portion to be treated.
(31) A kit for injecting a hyaluronic acid derivative which comprises the drug-introduced photo-crosslinked hyaluronic acid derived gel described in any one of (1) to (11), (18) and (19) being filled in an injection device capable of injecting said gel.

Effects of the Invention

According to the present invention, it can be provided a drug-introduced photo-crosslinked hyaluronic acid derived gel as a drug delivery system in which it can be directly administered to a diseased area such as a joint, an organ, etc., by an injection device such as an injection syringe, and by directly administering as mentioned above, a sufficient amount of a drug can be retained at an administered portion or diseased area, it has a sustained release property of a drug which can release the drug for a long period of time by staying at an administered site or a diseased area, and it is safe for a living body. The drug-introduced photo-crosslinked hyaluronic acid derived gel (hereinafter also referred to as "drug-introduced HA-gel") of the present invention can be administered directly to a diseased area by an injection device such as an injection syringe, etc., release of the drug at the administered site can be controlled, and sustained release of the drug is possible. Also, the drug-introduced HA-gel of the present invention is extremely useful for a medical use since it can be sterilized by a conventional manner such as moist-heat sterilization, etc., depending on the selection of the specific constitutional elements.

By using the drug-introduced HA-gel of the present invention which is capable of extruding with an injection device, it is possible not only to administer a drug to diseased area directly as a preparation for a local administration, but also to apply to various indication disease by selecting a drug. For example, when a drug-introduced HA-gel using non-steroidal anti-inflammatory drugs (NSAIDs) or disease-modifying anti-rheumatic drugs (DMARD) as a drug is directly administered into a knee joint cavity of a chronic arthritis patient such as knee osteoarthritis or chronic rheumatoid arthritis, then the drug-introduced HA-gel resides in the knee joint cavity or in a synovial tissue for a longer period of time and the drug is gradually released to the diseased area, so that a pain of the chronic knee arthritis patient can be reduced for a longer period of time. Also, for example, when carcinostatics, anticancer drugs, etc., are used as an introduced drug, by administering a carcinostatic-introduced photo-crosslinked hyaluronic acid gel directly to a cancer tissue, the carcinostatic can be gradually released only to the necessary portion without exerting any adverse effect to the other normal internal organs, and a patient can be relieved from a pain that is caused by side effects of taking carcinostatics for a long period of time.

As a basic concept of DDS, there is a function that a substrate takes up a drug molecule transferred to a portion to be required (delivery), and the drug molecule is released at a necessary portion (diseased area), but there are various protective responses or hindrances in a living body. Thus, even when a DDS agent having such a concept is, in fact, administered, it is disappeared or deactivated before reaching to the targeted diseased area, and further, even when it reaches to the diseased area, the drug is not released in almost all the cases. To the contrary, the drug-introduced HA-gel of the present invention is capable of extruding by an injection device, so that it is possible to carry out local administration to a joint, etc., and yet safety of the photo-crosslinked hyaluronic acid gel itself as a substrate is high, so that it has a property that it does not exert any adverse effect even when it resides in a living body for a longer period of time. By utilizing such properties, it is possible to carry out treatment by an effective means in which a drug is directly administered (injected) to an objective a diseased area without delivering it through a roundabout route, stayed said gel at the objective diseased area, and the drug is released gradually.

According to the above-mentioned method, a drug is not delivered by using a function of a living body but a drug-introduced HA-gel is directly administered to a diseased area, so that merits can be obtained that the drug can be surely reached to the diseased area, and yet it can reside at the portion suffered from a disease with the substrate as an anchor so that it can gradually release the drug from the portion for a longer period of time.

BEST MODE TO CARRY OUT THE INVENTION

In the following, the present invention is explained in detail.

The drug-introduced HA-gel of the present invention is a crosslinked hyaluronic acid having a crosslinked structure formed by binding with covalent bonds via photo-crosslinked group(s) between hyaluronic acids chains or in a hyaluronic acid molecule(s), and further a material retaining a drug or a derivative thereof by covalent bond(s) of a functional group(s) of the hyaluronic acid directly or via a spacer. The drug-introduced HA-gel of the present invention is prepared by introducing a photo-crosslinked group, and a drug or a derivative thereof into hyaluronic acid simultaneously or stepwisely to form a drug-introduced a photo-reactive hyaluronic acid derivative, and photo-crosslinking the drug-introduced photo-reactive hyaluronic acid derivative.

The hyaluronic acid to be used for the drug-containing HA-gel of the present invention is a polymer of a disaccharide unit comprising glucuronic acid and N-acetyl glucosamine, and the hyaluronic acid of the present invention contains its derivatives in the range which does not inhibit the effects of the present invention. Examples of such derivatives may be mentioned, for example, a hyaluronic acid derivative having a reducing end, an acetylated hyaluronic acid in which the hydroxyl groups in the hyaluronic acid are partially acetylated, etc.

Origin of the hyaluronic acid is not specifically limited, and either of the materials can be used including animal-derived hyaluronic acid such as chicken comb and umbilical cord, etc., hyaluronic acid prepared by using microorganisms which produces hyaluronic acid or prepared by genetic engineering, and chemically synthesized hyaluronic acid, etc. In particular, preferred are those which are highly purified, and substantially do not contain any material which is not permitted to be migrated as a medicine.

A molecular weight of the hyaluronic acid is not specifically limited, and as a weight average molecular weight, it is, for example, 10,000 to 5,000,000, preferably 100,000 to 3,000,000, and particularly preferably 600,000 to 1,500,000.

Incidentally, among the GAGs, effects of the present invention are more advantageously shown by the hyaluronic acid which is a polymer. That is, as mentioned above, it is common sense that as a polysaccharide is a higher molecular weight polymer substance, a solubility of the polysaccharide derivative into which a highly hydrophobic substance has been introduced is markedly lowered and insolubilized. Also, a hyaluronic acid with a higher molecular weight is likely gelled by a photo-crosslinking reaction. Accordingly, an effect of capable of maintaining characteristics that are injectable from an injection syringe, etc., by reducing an insolubilizing property caused by introduction of highly hydrophobic substance such as a drug, which can be obtained by applying the present invention, is more meaningful for a hyaluronic acid having a higher molecular weight.

The hyaluronic acid to be used in the present invention may be either in a free state in which no salt is formed, or in the state of a pharmaceutically acceptable salt. As the pharmaceutically acceptable salt of the hyaluronic acid, there may be mentioned, for example, an alkali metal ion salt such as a sodium salt, a potassium salt, etc., an alkaline earth metal ion salt such as a magnesium salt, a calcium salt, etc., a salt with an inorganic base such as an ammonium salt, etc., and an organic base such as a diethanolamine salt, a cyclohexylamine salt, amino acid salt, etc. In view of particularly high affinity to a living body, the hyaluronic acid salt is preferably a salt with an alkali metal ion, particularly preferably a salt with a sodium ion.

As a crosslinking group of the photo-crosslinked hyaluronic acid which is a base material of the drug-introduced HA-gel of the present invention, a photo-reactive crosslinking group (photo-reactive group) is used.

The photo-reactive group is a residue of a compound which occurs photodimerization reaction or photopolymerization reaction by irradiation with light (ultraviolet ray). It is not particularly limited so long as it is a residue of a compound which intermolecularly or intramolecularly crosslinks the hyaluronic acid(s) by irradiation with light as a photo-reactive group on the hyaluronic acid(s), and examples of such a compound may be preferably an olefin compound having a conjugated double bond(s). Specific examples may include cinnamic acid, a substituted cinnamic acid, acrylic acid, maleic acid, fumaric acid, sorbic acid, coumarin, thymine, etc. Among these, those having a vinylene group capable of forming a cyclobutane ring by light are preferred, and in view of photo-reactivity and safety, cinnamic acid and a substituted cinnamic acid are preferred. Examples of the substituted cinnamic acid may be mentioned a substituted cinnamic acid in which one or two hydrogens at any positions of the benzene ring of the cinnamic acid is/are substituted by a lower alkyl group (for example, methyl, ethyl, propyl, isopropyl, butyl, t-butyl, etc.), a lower alkoxy group (for example, methoxy, ethoxy, propoxy, isopropoxy, butoxy, etc.), amino group, hydroxyl group, etc. The substituted cinnamic acid is preferably aminocinnamic acid, particularly preferably p-aminocinnamic acid.

The photo-reactive group is bound to the carboxyl group or hydroxyl group of the hyaluronic acid through a covalent bond. A manner of bond is not specifically limited so long as the objects of the present invention have been accomplished, and it is preferably an ester bond or an amide bond, and an amide bond is most preferred. The photo-reactive group may be bound directly to the hyaluronic acid, but it is preferably bound to the hyaluronic acid through a spacer in view of improving photo-reactivity, making photo-crosslinked reaction easy, making a reaction of introducing the photo-reactive group into the polysaccharide easy, etc. Accordingly, a residue of a derivative (spacer derivative) in which a spacer is bound to cinnamic acid or a substituted cinnamic acid as a photo-reactive group is most preferred.

The compound which is a spacer as mentioned above is not specifically limited so long as it is a compound having two or more functional groups capable of bonding to the photo-reactive group and hyaluronic acid, preferably a compound having two or more functional groups selected from a carboxylic acid, a hydroxyl group and an amino group, and preferred examples may be mentioned, for example, an amino-alcohol ($H_2N$—$(CH_2)_n$—OH (n=1 to 18), $H_2N$—$(CH_2$—O$)_m$—H (m=2 to 9), etc.), a diamine ($H_2N$—$(CH_2)_l$—$NH_2$ (l=2 to 10), etc.), a diol (HO—$(CH_2)_k$—OH (k=2 to 10), etc.), an amino acid ($H_2N$—CHR—COOH(R: amino acid side chain), $H_2N$—$(CH_2)_j$—COOH (j=2 to 18)) and a peptide, etc.

The compound constituting a spacer as mentioned above is bound to hyaluronic acid, and then, the compound constituting a photo-reactive group may be bound, but it is preferred in view of easiness of the preparation that the compound constituting a spacer and the compound constituting a photo-reactive group are firstly bound, and then, the resulting compound is bound to hyaluronic acid. Preferred examples of the compound obtained by binding the above-mentioned compound constituting a spacer and the compound constituting a photo-reactive group may be mentioned, for example, a cinnamic acid aminoalkyl derivative (Ph-CH=CH—CO—O—$(CH_2)$ N—$NH_2$, Ph-CH=CH—CO—$(OCH_2)_n$—$NH_2$ (n and m are the same as defined above, Ph represents a phenyl group), etc.) in which aminoalcohol is bound to the carboxyl group of cinnamic acid through an ester bond, a cinnamic acid amide derivative (Ph-CH=CH—CO—NH—$(CH_2)$, —OH, Ph-CH=CH—CO—NH—$(CH_2O)_n$—OH (n and m are the same as defined above, Ph represents a phenyl group), etc.) in which aminoalcohol is bound to the carboxyl group of cinnamic acid through an amide bond, a cinnamic acid amide derivative (Ph-CH=CH—CO—NH—$(CH_2)_l$—$NH_2$ (l and Ph are the same as above), etc.) in which a diamine is bound to the carboxyl group of cinnamic acid through an amide bond, a cinnamic acid ester derivative (Ph-CH=CH—CO—O—$(CH_2)_k$—OH (k and Ph are the same as above), etc.) in which a diol is bound to the carboxyl group of cinnamic acid through an ester bond, a derivative (HOOC—CH=CH-Ph-NH—CO—CHR—$NH_2$ (R and Ph are the same as above), etc.) in which an amino acid or a peptide is bound to a substituted cinnamic acid (aminocinnamic acid) through an amide bond, etc., and preferably a derivative (cinnamic acid aminoalkyl) in which aminoalcohol is bound to the carboxyl group of cinnamic acid through an ester bond, and a cinnamic acid amide derivative in which aminoalcohol is bound to the carboxyl group of cinnamic acid through an amide bond. The aminoalcohol is preferably represented by the above-mentioned formula $H_2N$—$(CH_2)_n$—OH, n is 2 to 18, preferably 2 to 6, more preferably 2 to 4. Preferred example of the compound constituting a spacer may be mentioned aminoethanol, aminopropanol and aminobutanol, etc.

As a binding portion (a functional group of the hyaluronic acid) of the hyaluronic acid with a photo-reactive group or a spacer derivative to which a photo-reactive group is bound, a hydroxyl group or a carboxyl group may be mentioned, and a carboxyl group is more preferred in view of easiness in an introducing reaction of a photo-reactive group or a spacer derivative.

Also, a combination of a binding manner of a compound constituting a spacer and a compound constituting a photo-reactive group, and a binding manner of a compound constituting a spacer and a hyaluronic acid is not specifically limited, and any combination of bindings can be employed. For example, when cinnamic acid is used as the photo-reactive group and aminoalcohol is used as the spacer, a carboxyl group of the cinnamic acid and aminoalcohol are reacted to form an ester bond, and an amino group of the aminoalcohol and a carboxyl group of the hyaluronic acid are reacted to form an amide bond whereby the photo-reactive group may be bound to the hyaluronic acid through the spacer, or else, aminoalcohol is reacted to a carboxyl group of the cinnamic acid to form an amide bond, and a hydroxyl group of the aminoalcohol and a carboxyl group of the hyaluronic acid are reacted to form an ester bond, whereby the photo-reactive group may be bound to the hyaluronic acid through the spacer.

A drug to be introduced into the drug-introduced HA-gel of the present invention is not specifically limited so long as it is a drug having a functional group(s) to bind a carboxyl group or a hydroxyl group of the hyaluronic acid and capable of directly introducing into the hyaluronic acid through a covalent bonding, or a drug capable of binding via a spacer having a functional group(s) which can bind to a carboxyl group or a hydroxyl group of the hyaluronic acid. It is preferably a substance having a functional group(s) capable of binding to a carboxyl group or a hydroxyl group.

Examples of the drugs to be introduced into the drug-introduced HA-gel of the present invention may be mentioned non-steroidal anti-inflammatory drugs (NSAIDs) such as salicylic acid type non-steroidal anti-inflammatory drugs (salicylic acid, sazapirin, aspirin, diflunisal, salicylamide, etc.), fenamic acid type non-steroidal anti-inflammatory drugs (flufenamic acid, aluminum flufenamate, mefenamic acid, floctafenine, tolfenamic acid, etc.), arylacetate type non-steroidal anti-inflammatory drugs (felbinac, diclofenac, tolmetin sodium, sulindac, fenbufen, indometacin, indometacin farnesyl, acemetacin, proglumetacin maleate, amfenac sodium, nabumetone, mofezolac, etodolac, alclofenac, etc.), propionic acid type non-steroidal anti-inflammatory drugs (ibuprofen, flurbiprofen, ketoprofen, naproxen, pranoprofen, fenoprofen, tiaprofenic acid, oxaprozin, loxoprofen sodium, alminoprofen, zaltoprofen, tiaprofenic acid, etc.), pyrazolone type non-steroidal anti-inflammatory drugs (ketophenyl butazone, etc.), oxicam type non-steroidal anti-inflammatory drugs (piroxicam, tenoxicam, ampiroxicam, etc.), other non-steroidal anti-inflammatory drugs (tiaramide hydrochloride, tinoridine hydrochloride, benzydamine hydrochloride, epirizole, emorfazone, tolmetin, diflunisal, acetaminophen, floctafenine, tinoridine, etc.), etc.; cyclooxygenase-2 inhibitor; disease-modifying anti-rheumatic drugs (DMARD) such as penicillamine, lobenzarit disodium, auranofin, bucillamine, actarit, salazosulfapyridine, sodium aurothiomalate, chloroquine, TNFα acceptor preparation, mizoribine, cyclosporine, methotrexate, leflunomide, azathioprine, anti-TNFα antibody, anti-IL-6 acceptor antibody, anti-CD4 antibody, IL-1 acceptor antagonist, anti-CD52 antibody, p38MAP kinase inhibitor, ICE inhibitor, TACE inhibitor, etc.; steroid drugs such as cortisone acetate, hydrocortisone, prednisolone, methylprednisolone, triamcifulone, triamcifulone acetonide, dexamethasone, dexamethasone palmitate, betamethasone, paramethasone acetate, halopredone acetate, prednisolone farnesylate, tetracosactide acetate, etc.; local anesthetics such as procaine hydrochloride, tetracaine hydrochloride, lidocaine hydrochloride, etc.; matrix metalloproteinase (MMP) inhibitors such as hydroxamic acid, etc.; allergic diseases treating drugs such as xanthine analogue drugs (theophylline, etc.), anti-allergic drugs (fexoquinadine, epinastatine, cetirizine, ketotifen, sodium cromoglycate, pemirolast, etc.), anti-histaminic drugs (fexoquinadine, cetirizine, etc.), etc.; anti-cancer drugs such as irinotecan, 5-fluorouracil, etc., and the like, but the invention is not limited by these. As the preferred drugs, there may be mentioned non-steroidal anti-inflammatory drugs, disease-modifying anti-rheumatic drugs, MMP inhibitor, steroid drugs, and anti-cancer drugs, of these, non-steroidal anti-inflammatory drugs, disease-modifying anti-rheumatic drugs, and anti-cancer drugs are preferably mentioned.

When a drug is introduced into the hyaluronic acid via a spacer, said compound constituting a spacer has both of a functional group(s) which binds to the hyaluronic acid and a functional group(s) which binds to the drug and it may have a plural number of these functional groups. The functional group(s) of said spacer can be selected variously depending on a binding manner of the hyaluronic acid and the drug, and a binding manner of said spacer with the hyaluronic acid and the drug is preferably an ester bond or an amide bond. Also, a combination of a binding manner of the compound constituting a spacer and the drug, and a binding manner of the compound constituting a spacer and the hyaluronic acid is not specifically limited, and bindings of an optional combination can be employed.

For example, when a spacer is introduced by an amide bond with a carboxyl group of the hyaluronic acid, a spacer having an amino group can be selected. When a spacer is introduced by an ester bond with a carboxyl group or a hydroxyl group of the hyaluronic acid, a spacer having a hydroxyl group or a carboxyl group can be selected. A manner of binding between a drug and a spacer is the same, and, for example, in the case of a drug having a hydroxyl group or a carboxyl group, if a spacer having a carboxyl group or a hydroxyl group is selected, then, the drug can be introduced by an ester bond, and if a spacer having an amino group is selected, then, it can be introduced by an amide bond.

Also, when a drug-introduced HA-gel is injected into a living body, it is more preferably required that the drug be gradually freed and released from the hyaluronic acid chain in a living body. It can be considered that the drug be gradually released in comply with decomposition of a photo-crosslinked hyaluronic acid derivative, and in particular, it is desired that a binding portion of a drug and a spacer be biodegraded. By changing a binding manner between the drug and the spacer, resistance to biodegradation can be controlled, whereby it is possible to control a sustained release rate. For example, when hydrolysis occurred in a living body is considered, an ester bond is likely decomposed than an amide bond. Thus, when a spacer which forms an amide bond with a hyaluronic acid and forms an ester bond with a drug is selected, a drug-introduced HA-gel injected into a living body likely releases a drug from a hyaluronic acid chain by hydrolysis. Similarly, when a drug is directly introduced into a hyaluronic acid, it is preferred to introduce the drug into hyaluronic acid through an ester bond in view of hydrolysis in a living body.

A spacer to be used for biding a drug and a hyaluronic acid of a drug-introduced HA-gel according to the present invention can be selected in view of the above-mentioned points, and it is not particularly limited so long as it can bind a drug and a hyaluronic acid and can accomplish the objects of the present invention. With regard to a preferred example of the compound constituting a spacer, those mentioned for introduction of the photo-reactive group as above can be similarly mentioned. Aminoalcohol is more preferred, and there may be mentioned, for example, aminoethanol, aminopropanol and aminobutanol, etc.

The compound constituting a spacer as mentioned above may firstly bind the spacer to a hyaluronic acid similarly as in the introduction of the photo-reactive group, and then, a drug may bind to the hyaluronic acid to which the spacer has bound, but it is more preferred to synthesize a bound product of the compound constituting a spacer and a drug previously, and then, the obtained compound is bound to a hyaluronic acid in view of easiness of preparation.

Also, a binding portion (a functional group(s) of a hyaluronic acid) of the hyaluronic acid with a drug or a spacer may be a hydroxyl group similarly as in the introduction of the photo-reactive group, but a carboxyl group is more preferred in view of easiness in introducing reaction of the drug or the spacer.

Incidentally, in the following descriptions, if it is not clearly described whether introduction of a photo-reactive group and a drug into a hyaluronic acid is carried out directly or via a spacer, either of which is basically included in the present invention. That is, a photo-reactive group and a drug each contain a photo-reactive group derivative having a spacer portion and a drug derivative having a spacer portion.

In the preparation of a drug-introduced HA-gel according to the present invention, firstly a drug-introduced photo-reactive hyaluronic acid derivative in which a photo-reactive group and a drug are introduced in a hyaluronic acid and is soluble in an aqueous medium is prepared as an intermediate product, and then, an aqueous solution of said drug-introduced photo-reactive hyaluronic acid derivative is photoirradiated to cause crosslinking. The water-soluble drug-introduced photo-reactive hyaluronic acid derivative which is an intermediate product can be prepared by introducing a photo-reactive group and/or a drug into a hyaluronic acid, thereafter subjecting the product to an alkali treatment.

For introducing a drug and a photo-reactive group into a hyaluronic acid, any of the methods may be employed wherein a method in which a photo-reactive group is introduced into a hyaluronic acid and then a drug is introduced, a method in which a drug is introduced and then a photo-reactive group is introduced, or a method in which a drug and a photo-reactive group are simultaneously introduced. When either one of a drug or a photo-reactive group is previously introduced, any of the methods may be employed wherein a method in which after introducing a drug or a photo-reactive group, the product is isolated by a post-treatment, and then, the other is introduced, or a method in which they are introduced one after another successively in one pot reaction. In the case of the former method, whereas it requires troublesome operation or time in preparation steps, there is a merit that degree of substitution of the drug and the photo-reactive group can be precisely controlled, and in the case of the latter method, there is a merit that the objective product can be effectively obtained without requiring troublesome operation or time for a reaction.

As mentioned above, the photo-reactive group or the drug can bind to either of a carboxyl group or a hydroxyl group of hyaluronic acid, and in view of the reactivity possessed by the functional group(s), it is easy to bind to the carboxyl group and is preferred. As a method of accomplishing such a binding, there may be mentioned, for example, a method of using a water-soluble condensing agent such as a water-soluble carbodiimide (for example, 1-ethyl-3-(3-dimethylaminopropyl)carbodiimide hydrochloride (EDCI.HCl), 1-cyclohexyl-3-(2-morpholinoethyl)carbodiimide-meto-p-toluene-sulfonate, 1-cyclohexyl-3-(2-morpholinoethyl)-carbodiimide hydrochloride, etc.), etc., a method of using an auxiliary condensing agent such as N-hydroxysuccinimide (HOSu) or N-hydroxybenzotriazole (HOBt), etc. with the above-mentioned condensing agent, an active esterification method, an acid anhydride method, etc. Of these, as a reaction in the presence of an aqueous medium, preferred is a method of using a water-soluble condensing agent or a method of using a reaction assistant and a water-soluble condensing agent. In particular, more preferred is a method of using a reaction assistant and a water-soluble condensing agent in view of inhibiting side reaction. As the aqueous medium, in addition to a sole solvent of water, there may be mentioned a mixed solvent of water and a water-miscible organic solvent such as dioxane, dimethyl-formamide (DMF), acetone, alcohol (methanol, ethanol, etc.), etc. As mentioned above, the carboxyl group of hyaluronic acid and the photo-reactive group or the drug are preferably bound through an ester bond or an amide bond.

In the drug-introduced HA-gel of the present invention, a degree of substitution of the photo-reactive group and the drug into the hyaluronic acid are not particularly limited so long as solubility of the drug-introduced photo-reactive hyaluronic acid derivative in an aqueous medium can be retained, and further, a drug-introduced HA-gel obtained by photo-crosslinking the same can retain the characteristics that are capable of extruding by an injection device. In other words, a degree of substitution is required to be selected so that these conditions are satisfied.

In the present specification, the degree of substitution means an introducing rate (percentage) of a drug or a photo-reactive group based on disaccharide unit of the hyaluronic acid. For example, when a drug is to be introduced into a carboxyl group of a hyaluronic acid, an degree of substitution of the drug being 10% means that 10 drugs are introduced per 100 disaccharide units of said hyaluronic acid chain. As a matter of course, drugs can be substituted at respective carboxyl groups which are in adjacent disaccharide units.

Degree of substitution of the photo-reactive group and the drug can be controlled by changing reaction conditions such as charged amounts of a condensing agent, an auxiliary condensing agent, a photo-reactive group and a drug, or a reaction solvent, a reaction temperature, etc., and suitable introducing ratios of the photo-reactive group and the drug are determined in consideration of an amount of the photo-reactive group necessary for the later cross-linking reaction, or an amount of the drug necessary for the diseased portion to be administered to a living body or a sustained release efficiency thereof, etc.

A degree of substitution of the drug is generally 1 to 60 mol %, preferably 5 to 30 mol %, more preferably 5 to mol %, particularly preferably 7 to 20 mol % based on a molar number of a repeating disaccharide unit of the hyaluronic acid. A degree of substitution of the photo-reactive group is generally 5 to 50 mol %, preferably 5 to mol %, more preferably 5 to 20 mol %, and particularly preferably 8 to 20 mol %. Moreover, a total degree of substitution in sum of the photo-reactive group and the drug is generally 6 to 60 mol %, preferably 10 to 50 mol %, more preferably 10 to 45 mol %, and particularly preferably 15 to 40 mol %. It is more desired that the photo-reactive group and the drug are each introduced with suitable ratios in these ranges. Amounts of the photo-reactive group and the drug introduced can be measured by, for example, a measurement of an absorbance or by a method of HPLC, NMR, etc.

It is preferred to further treat the drug-introduced photo-reactive hyaluronic acid derivative prepared as mentioned above with an alkali. The alkali treatment which makes the reaction solution after introducing reaction alkaline is not specifically limited so long as it is a treatment that makes said solution alkaline.

More specifically, there may be exemplified by a method in which either of an organic base or an inorganic base is added to said solution as an alkali treatment, and a method of using an inorganic base is more preferred in view of the treatment after said treatment, etc. Moreover, among inorganic bases, weak bases such as sodium hydrogen carbonate or sodium carbonate are more desired than strong bases such as sodium hydroxide since the former has a possibility of less affecting to the hyaluronic acid or the drug. pH conditions of the alkali treatment herein mentioned are exemplified by 7.2 to 11, preferably 7.5 to 10.

A treatment time of the alkali treatment is not particularly limited so long as it does not cause conversion of the hyaluronic acid to low-molecular compound, and may be mentioned for 2 to 12 hours, preferably 2 to 6 hours. When the treatment is carried out for the above-mentioned time, a soluble drug-introduced photo-reactive hyaluronic acid derivative can be obtained without causing any effects on the hyaluronic acid.

That is, as an example, a soluble drug-introduced photo-reactive hyaluronic acid derivative can be obtained by adding weak alkali such as sodium hydrogen carbonate, etc. to a reaction solution in which a drug and a photoreactive group are introduced into a hyaluronic acid, subjecting to mixing treatment of the mixture for several hours, and subjecting to post-treatments such as ethanol precipitation, drying, etc.

In general, when the above-mentioned photo-reactive group and the drug are introduced into the carboxyl group of the hyaluronic acid, said carboxyl group is lowered in its hydrophilic property by a substitution reaction to an amide bond or an ester bond, but by carrying out the above-mentioned alkali treatment, even when introducing amounts of the photo-reactive group and the drug, in particular an introducing amount of the drug is/are made a larger amount which could not be accomplished in the conventional techniques, it is possible to maintain the solubility of the drug-introduced photo-reactive hyaluronic acid derivative in an aqueous medium (it retains the same solubility as that of the starting hyaluronic acid).

Light is irradiated to the drug-introduced photo-reactive hyaluronic acid derivative prepared as mentioned above to cause crosslinking, a drug-introduced HA-gel of the present invention can be prepared. That is, the drug-introduced photo-reactive hyaluronic acid derivative prepared as mentioned above is isolated and dissolved in an aqueous medium to prepare an aqueous solution thereof, and then, the aqueous solution is applied to photoirradiation to cause crosslinking. The aqueous medium to be used for preparing the solution is not particularly limited so long as it does not cause any effect on a living body, and further does not cause any effect on the photo-crosslinking reaction at a later step, and a physiological saline or phosphate buffered physiological saline is desired. A concentration of the drug-introduced photo-reactive hyaluronic acid derivative in the above-mentioned aqueous solution is, in terms of % by weight, generally 0.1% to 10%, more preferably 0.5% to 3%, further preferably 0.5% to 1.5% for obtaining a drug-introduced HA-gel having a characteristic that is capable of extruding by an injection device.

As mentioned above, as one of merits to isolate the drug-introduced photo-reactive hyaluronic acid derivative as an intermediate product, by dissolving the drug-containing photo-reactive hyaluronic acid derivative in an aqueous solvent such as a buffer, etc., to once form a uniform aqueous solution state, and by subjecting to photoirradiation and crosslinking at this state, it is possible to carry out crosslinking with a hydrated state, i.e., with a state that much water molecules are hydrated to hyaluronic acid chains, whereby a gel having characteristics that are capable of extruding by an injection device can be finally formed. Also, as a merit on the preparation, there are mentioned that since said intermediate product is once purified and isolated, it is possible to remove impurities such as unreacted material or a condensing agent, etc., and further since said drug-introduced photo-reactive hyaluronic acid derivative is soluble in an aqueous medium, after making an aqueous solution, it is sometimes possible to carry out sterilization, elimination of bacteria or removal of alien substances by filtering said aqueous solution.

Photoirradiation to an aqueous solution of the drug-introduced photo-reactive hyaluronic acid derivative may be carried out in any form, and it is desired to fill an aqueous drug-introduced photo-reactive hyaluronic acid derivative solution in a glass syringe and then to carry out photoirradiation. For example, when a cinnamic acid derivative is used as a photo-reactive group, after photo-irradiation, cinnamic acids form a dimer so that hyaluronic acid chains take a crosslinked structure. When a ultraviolet lamp such as a high pressure mercury lamp, a metal halide lamp, etc. is used as a light source, and if a glass syringe is used, the glass itself acts as a cut filter by cutting a wavelength which causes adverse effects on the hyaluronic acid, and transmitting a wavelength necessary for photoreaction.

The crosslinked drug-introduced HA-gel obtained by photoirradiating to the above-mentioned aqueous drug-introduced photo-reactive hyaluronic acid derivative solution crosslinks while containing or including a water molecule(s) therein, so that it takes a gel state structure, and has characteristics that are capable of extruding from an injection needle, etc.

In the present invention, characteristics "that are capable of extruding from an injection device" mean characteristics that can extrude the drug-introduced HA-gel of the present invention from an injection needle mounted on a generally used injection syringe for medical use filled with the drug-introduced HA-gel of the present invention not with a pressure by a machine but a pressure which can be obtained by a usual manual operation of a human (general adult), and are capable of infusing in an objective such as a living body, etc. More specifically, it means characteristics that are capable of extruding, for example, with a pressure of 0.5 to 5 kg/cm$^2$, preferably 0.5 to 2 kg/cm$^2$ or so from an injection syringe mounted with an injection needle having 20 (outer diameter: 0.90 mm, inner diameter: 0.66 mm) to 27 (outer diameter: 0.40 mm, inner diameter: 0.22 mm) gauge, preferably 20 to 25 (outer diameter: 0.50 mm, inner diameter: 0.32 mm) gauge, more preferably 23 (outer diameter: 0.65 mm, inner diameter: 0.40 mm) to 25 gauge at a room temperature neighbor to 25° C. Of course, a pressurization to obtain the pressure mentioned in the above-mentioned definition may be pressurization by a machine or pressurization by a manual operation of a human. Also, as the generally used injection syringe for medical use, there may be mentioned an injection syringe used for a medical treatment or animal experiment, etc., and there may be mentioned, for example, an injection syringe having a diameter of 14 mm, a syringe length of 58 mm, and a volume of 5 ml (for example, 5 Ml syringe available from TERUMO corporation). For example, when the above-mentioned injection needle (for example, 20 to 25 gauge) is mounted on the injection syringe, and for extrude the drug-introduced HA-gel of the present invention filled therein in an amount of 5 ml, it takes 1 second to 5 minutes with the above-mentioned pressure (for example, 0.5 to 5 kg/cm$^2$). The characteristics "that are capable of extruding from an injection device" of the drug-introduced HA-gel are not necessary corresponding to the viscosity of the drug-introduced HA-gel in strict meaning. However, if the viscosity of the drug-introduced HA-gel is considered as a measure of the characteristics "that are capable of extruding from an injection device" according to the present invention, said characteristics correspond to a viscosity of preferably 1 to 50 Pa·s, more preferably 3 to 40 Pa·s, further preferably 3 to 35 Pa·s or so, which are measured by using a rotation viscometer and a standard cone (1°34', 1 rpm) at 20° C.

The drug-introduced HA-gel of the present invention has the above-mentioned characteristics so that it can be made a preparation for local administration or a preparation for non-oral administration in which the drug-containing HA-gel is administered to an objective (a living body, etc.) by infusion or injection.

Moreover, the present invention can be also provided an injection device in which the drug-introduced HA-gel is filled in the injection device and sealed with a gasket, or a kit having said injection device and a plunger for extruding the drug, etc.

For example, when the NSAIDs-introduced HA-gel is used as a preparation for local administration, metabolism by a digestive organ system or side effects against digestive organs can be avoided, whereby more efficient and more safety treatment effects can be expected.

A residual property of the thus cross-linked drug-introduced HA-gel in a living body can be further elongated than that of the hyaluronic acid into which a drug is introduced by crosslinking, and the residual property can be controlled by changing the degree of crosslinking (a crosslinking ratio).

Since the drug has been introduced into the photo-crosslinked hyaluronic acid by a covalent bond, the drug is not rapidly released immediately after administration, but gradually released accompanying decomposition of the photo-crosslinked hyaluronic acid which is a basic material, or dissociation of the bond between the photo-crosslinked hyaluronic acid and the drug. Thus, a sustained release time can be elongated by preparing a drug-introduced HA-gel having a high residual property, i.e., having a high crosslinking ratio.

The drug-introduced HA-gel of the present invention not only shows a function as a carrier having a drug-sustained release property which releases the drug by staying at the administered portion for a long period of time, but also is expected to show lubricating action inherently possessed by the hyaluronic acid when it is administered, for example, to a portion suffered from joint diseases.

As mentioned above, for the drug-introduced photo-reactive hyaluronic acid derivative which is an intermediate product for preparing a drug-introduced HA-gel of the present invention to be water-soluble, and for the drug-introduced HA-gel to have a characteristic that is capable of extruding from an injection device, in addition to obtain the drug-introduced photo-reactive hyaluronic acid derivative by an alkali treatment, it is necessary to suitably select mainly a molecular weight of the hyaluronic acid, kinds and degree of substitution of the photo-reactive group and the drug, a concentration of the drug-introduced photo-reactive hyaluronic acid derivative in an aqueous solution thereof at the time of crosslinking, etc., whereby a material having desired characteristics can be prepared. Accordingly, for determining specific constitutions of the drug-introduced HA-gel according to the present invention, the above-mentioned elements are suitably selected in view of the required drug. From such viewpoints, the following ((1) to (14)) are mentioned as specific embodiments of the drug-introduced HA-gel according to the present invention. However, the present invention is not limited by these.

(1) A drug-introduced HA-gel of the present invention wherein the molecular weight of the hyaluronic acid is 10,000 to 5,000,000, the degree of substitution of the photo-reactive group is 5 to 50 mol % based on disaccharide unit of the hyaluronic acid (hereinafter the same), the degree of substitution of the drug is 1 to 60 mol %, and the sum of the degree of substitution of the photo-reactive group and the drug is 6 to 60 mol %.

(2) A drug-introduced HA-gel of the present invention wherein the molecular weight of the hyaluronic acid is 10,000 to 3,000,000, the degree of substitution of the photo-reactive group is 5 to 30 mol %, the degree of substitution of the drug is 5 to 30 mol %, and the sum of the degree of substitution of the photo-reactive group and the drug is 10 to 50 mol %.

(3) A drug-introduced HA-gel of the present invention wherein the molecular weight of the hyaluronic acid is 600,000 to 1,500,000, the degree of substitution of the photo-reactive group is 5 to 20 mol %, the degree of substitution of the drug is 5 to 25 mol %, and the sum of the degree of substitution of the photo-reactive group and the drug is 10 to 45%.

(4) A drug-introduced HA-gel of the present invention wherein the molecular weight of the hyaluronic acid is 600,000 to 1,500,000, the degree of substitution of the photo-reactive group is 5 to 20 mol %, the degree of substitution of the drug is 5 to 25 mol %, the sum of the degree of substitution of the photo-reactive group and the drug is 10 to 45 mol %, and the molecular weight of the drug is 100 to 500.

(5) A drug-introduced HA-gel of the present invention wherein the molecular weight of the hyaluronic acid is 800,000 to 1,200,000, the degree of substitution of the photo-reactive group is 5 to 20%, the degree of substitution of the drug is 5 to 25%, and the sum of the degree of substitution of the photo-reactive group and the drug is 10 to 45%.

(6) A drug-introduced HA-gel of the present invention of the above-mentioned (3) to (5), wherein it is obtainable by photo-crosslinking while making a concentration of the solution of the drug-introduced photo-reactive hyaluronic acid derivative 0.5 to 3% by weight.

(7) A drug-introduced HA-gel of the present invention, wherein the molecular weight of the hyaluronic acid is 800,000 to 1,200,000, the degree of substitution of the photo-reactive group is 8 to 20 mol %, the degree of substitution of the drug is 7 to 20 mol %, the sum of the degree of substitution of the photo-reactive group and the drug is 15 to 40 mol %, and the drug is a drug selected from NSAIDs and DMARD.

(8) A drug-introduced HA-gel of the present invention, the molecular weight of the hyaluronic acid is 800,000 to 1,200,000, the degree of substitution of the photo-reactive group is 8 to 20 mol %, the degree of substitution of the drug is 7 to 20 mol %, the sum of the degree of substitution of the photo-reactive group and the drug is 15 to 40 mol %, and the drug is anti-cancer drugs.

(9) A drug-introduced HA-gel of the present invention, the molecular weight of the hyaluronic acid is 800,000 to 1,200,000, the degree of substitution of the photo-reactive group is 8 to 20 mol %, the degree of substitution of the drug is 7 to 20 mol %, the sum of the degree of substitution of the photo-reactive group and the drug is 15 to 40 mol %, and the drug is a drug selected from naproxen, ibuprofen, flurbiprofen, felbinac, diclofenac, etodolac and actarit.

(10) The drug-introduced HA-gel of the present invention of the above-mentioned (7) to (9), wherein it is obtainable by photo-crosslinking while making a concentration of the solution of the drug-introduced photo-reactive hyaluronic acid derivative 0.5 to 1.5% by weight.

(11) A drug-introduced HA-gel of the present invention in which a photo-reactive group (photo-crosslinked group) binds to a spacer through an ester bond, the photo-reactive group (photo-crosslinked group)-bound spacer binds to a carboxyl group of hyaluronic acid by an amide bond, a drug binds to the spacer through an ester bond and the drug-bound spacer binds to a carboxyl group of hyaluronic acid by an amide bond.

(12) The drug-introduced HA-gel according to the above-mentioned (11) of the present invention, wherein the spacer is aminoalcohol, and the photo-reactive group is cinnamic acid or a substituted cinnamic acid.

(13) The drug-introduced HA-gel of the present invention mentioned in the above (11), wherein the spacer is an aminoalcohol selected from aminoethanol, aminopropanol and aminobutanol, the photo-reactive group is cinnamic acid or aminocinnamic acid, the molecular weight of the hyaluronic acid is 800,000 to 1,200,000, the degree of substitution of the photo-reactive group is 5 to 20%, the degree of substitution of the drug is 5 to 25%, and the sum of the degree of substitution of the photo-reactive group and the drug is 10 to 45%.

(14) The drug-introduced HA-gel of the present invention mentioned in the above (13), wherein it can be obtainable by photo-crosslinking by making a concentration of a solution of the drug-introduced photo-reactive hyaluronic acid derivative 0.5 to 1.5% by weight.

EXAMPLES

Hereinafter, the present invention is explained more concretely by referring to Examples, but the present invention is not limited by these.

Preparation Example 1

Synthesis of t-butoxycarbonyl-aminopropanol (Boc-aminopropanol)

In 10 mL of dichloromethane was dissolved 1.542 g (20.5 mmol) of aminopropanol, and 4.484 g (20.5 mmol) of di-t-butyldicarbonate ($Boc_2O$)/10 mL of dichloromethane solution was gradually added dropwise to the solution under ice-cooling. Thereafter, the reaction mixture was brought to room temperature, the mixture was stirred for 2 hours and 40 minutes, and after disappearance of the starting materials was confirmed by thin-layer chromatography (hereinafter also referred to as TLC), dichloromethane was distilled off under reduced pressure. The reaction proceeded quantitatively and Boc-aminopropanol as an oil was obtained with a yielded amount of 3.92 g. The structure was identified by $^1$H-NMR ($CDCl_3$).

$^1$H-NMR (500 MHz, $CDCl_3$) δ (ppm): 1.46 (9H, s, Boc), 1.66 (2H, quant, —$NHCH_2CH_2CH_2O$—), 3.27 (3H, m, —$NHCH_2CH_2CH_2O$—), 3.66 (2H, m, —$NHCH_2CH_2CH_2O$—), 4.91 (1H, br, $CH_2OH$).

Preparation Example 2

Synthesis of Aminopropyl Cinnamate Hydrochloride

To 1.21 g (6.9 mmol) of t-butoxycarbonyl-amino-propanol was added 6 mL of chloroform, and 956 μL (6.9 mmol) of triethylamine, 1.15 g (6.9 mmol) of cynnamoyl chloride and 253 mg (2.1 mmol) of 4-dimethylaminopyridine were successively added to the mixture under ice-cooling. After stirring the mixture at room temperature for 20 minutes, ethyl acetate was added to the reaction mixture, the resulting mixture was subjected to washing by separatory funnel twice with 5% aqueous citric acid solution, with water, twice with 5% aqueous sodium hydrogen carbonate solution, with water, and with saturated saline and separated, and then, the organic layer was dried over anhydrous sodium sulfate. The sodium sulfate was filtered off, and the filtrate was concentrated under reduced pressure to give white solid. The precipitated white solid was washed with hexane, and dried under reduced pressure to obtain 1.38 g (Yield: 65%) of Compound (1-1). Then, to 860 mg (2.8 mmol) of Compound (1-1) was added 6 Ml of 4M hydrogen chloride/dioxane solution under ice-cooling and the mixture was stirred at room temperature for 35 minutes. The mixture was dried under reduced pressure to obtain aminopropyl cinnamate hydrochloride as white crystal.
Yield: 76%.

Example 1

Synthesis of Aminopropyl Cinnamate-Introduced Sodium Hyaluronate (Hereinafter Also Referred to as Photo-Reactive HA)

In 115 mL of water/144 mL of dioxane was dissolved 1.0 g (2.5 mmol/disaccharide unit (a molar number as a disaccharide unit (hereinafter the same). In the following, this sodium hyaluronate is also referred to as HA.) of sodium hyaluronate having a weight average molecular weight of 900,000, then, 172 mg of N-hydroxysuccinimide (hereinafter also referred to as HOSu.)/5 mL of water, 143 mg of water-soluble carbodiimide hydrochloride (hereinafter also referred to as WSCI. HCl.)/5 mL of water, and 181 mg of aminopropyl cinnamate hydrochloride/5 mL of water were successively added, and then, the mixture was reacted under stirring for 3 hours and 30 minutes. Subsequently, 10 mL of 7.5% aqueous sodium hydrogen carbonate solution was added to the reaction mixture, and after stirring for 2 hours and 50 minutes, 214 mg of acetic acid/2 mL of water was added to the mixture to neutralize the same, then, 1 g of sodium chloride was added thereto and the mixture was stirred. To the mixture was added 500 mL of ethanol to cause precipitation, and to the resulting precipitate was added 150 mL of ethanol to carry out decantation twice, the precipitate was washed twice with 95% ethanol, dried at 40° C. under reduced pressure overnight, to obtain 1.0 g of aminopropyl cinnamate-introduced HA (photo-reactive HA) as white solid. The degree of substitution of the cinnamic acid was 16.2%.

Example 2

Synthesis of Naproxen-Introduced Photo-Cross-Linked Sodium Hyaluronate Gel (1) Synthesis of aminopropyl-naproxen(ester)hydrochloride In 2 mL of dichloromethane were dissolved 350 mg (2 mmol) of Boc-aminopropanol obtained in Preparation example 1 and 462 mg (2 mmol) of naproxen, and 48 mg (0.4 mmol) of N,N-dimethylaminopyridine (hereinafter also referred to as DMAP), and 422 mg (2.2 mmol) of WSCI. HCl/2 mL of dichloromethane were successively added thereto under ice-cooling. The reaction mixture was brought to room temperature and stirred for 4 hours and 50 minutes. Then, dichloromethane was distilled off under reduced pressure, ethyl acetate was further added to the residue, and the mixture was successively subjected to washing by separatory funnel twice with 5% citric acid, twice with water and 5% sodium hydrogen carbonate, and further with water and saturated saline. The mixture was dehydrated and dried over sodium sulfate, and ethyl acetate was distilled off under reduced pressure to obtain 720 mg of Boc-aminopropyl-naproxen as white crystal (Yield: 93%). The structure was identified by $^1$H-NMR ($CDCl_3$).

$^1$H-NMR (500 MHz, $CDCl_3$) δ (ppm): 1.42 (9H, s, Boc), 1.58 (3H, d, —$OCOCH(CH_3)$—), 1.75 (2H, quant, —$NHCH_2CH_2CH_2O$—), 3.07 (2H, m, —$NHCH_2CH_2CH_2O$—), 3.85 (1H, q, —$OCOCH(CH_3)$—), 3.91 (3H, s, —$OCH_3$), 4.13 (2H, m, —$NHCH_2CH_2CH_2O$—), 4.63 (1H, br, —$NHCH_2$—), 7.09-7.75 (6H, m, Aromatic H).

In 1 mL of dichloromethane was dissolved 684 mg (1.76 mmol) of the obtained Boc-aminopropyl-naproxen, 2 mL of 4N-Hydrogen chloride in Ethyl acetate (available from WATANABE CHEMICAL INDUSTRIES, LTD.) was added thereto under ice-cooling, and the mixture was stirred under ice-cooling for 20 minutes, and then, at room temperature for 1 hour. After disappearance of Boc-aminopropyl-naproxen was confirmed by TLC, diethyl ether was added to the reaction mixture and decantation was carried out three times. Then, the mixture was dried under reduced pressure to obtain aminopropyl-naproxen (ester) hydrochloride (Yielded amount: 564 mg). The structure was identified by $^1$H-NMR (CDCl$_3$).

$^1$H-NMR (500 MHz, CDCl$_3$+CD$_3$OD) δ (ppm): 1.57 (3H, d, —OCOCH(C$\underline{H}_3$)—), 2.02 (2H, quant, —NHCH$_2$C$\underline{H}_2$CH$_2$O—), 2.88 (2H, m, —NHC$\underline{H}_2$CH$_2$CH$_2$O—), 3.87 (1H, q, —OCOC$\underline{H}$(CH$_3$)—), 3.90 (3H, S, —OCH$_3$), 4.17 (2H, m, —NHCH$_2$CH$_2$C$\underline{H}_2$O—), 7.08-7.73 (6H, m, Aromatic H), 8.10 (br, H$_3$N$^+$C$\underline{H}_2$—).

(2) Synthesis of Naproxen-Introduced Photo-Crosslinked Sodium Hyaluronate Gel (Naproxen-Introduced Photo-Cross-Linked HA Gel)

In a solution of 11.5 mL of water/11.5 mL of dioxane was dissolved 100 mg (0.25 mmol/disaccharide unit) of aminopropyl cinnamate-introduced HA (photo-reactive HA) obtained in Example 1, 0.1 mL of 1 mol/L HOSu, 0.1 mL of 0.5 mol/L WSCI.HCl, and 0.1 mL of 0.5 mol/L aminopropyl-naproxen (ester) hydrochloride obtained in the above-mentioned (1) were successively added to the solution, and the resulting mixture was stirred over day and night to carry out the reaction. To the reaction mixture was added 1.5 mL of a 5% aqueous sodium hydrogen carbonate solution, and the mixture was stirred for 4 hours. Then, 43 μL of 50% acetic acid was added to the mixture to neutralize the same, and then, 620 mg of sodium chloride was added to the mixture and the mixture was stirred. 50 mL of ethanol was added to the mixture to cause precipitation, washed twice with 80% ethanol, twice with ethanol, and once with diethyl ether, and the mixture was dried under reduced pressure overnight to obtain 83 mg of naproxen-introduced photo-reactive HA as white solid. The degree of substitution of naproxen was 9.3%.

A 1% phosphate buffered physiological saline solution of the obtained naproxen-introduced photo-reactive HA (photo-reactive group: cinnamic acid) was prepared, and filled in a 5 mL glass syringe. The filled syringe was photoirradiated with a 3 kw metal halide lamp, to obtain a naproxen-introduced photo-crosslinked HA gel. Moreover, the syringe filled with the naproxen-introduced photo-crosslinked HA gel was subjected to heat treatment at 121° C. for 20 minutes. When a viscosity thereof was measured by using a rotation viscometer at 20° C., it was 34.7 Pa·s with a standard cone (1°34', 1 rpm).

Example 3

Synthesis of Ibuprofen-Introduced Photo-Cross-Linked Sodium Hyaluronate Gel (1) Synthesis of aminopropyl-ibuprofen(ester)hydrochloride In 2 mL of dichloromethane were dissolved 352 mg (2 mmol) of Boc-aminopropanol obtained in Preparation example 1 and 412 mg (2 mmol) of ibuprofen, and 48 mg (0.4 mmol) of DMAP and 423 mg (2.2 mmol) of WSCI.HCl/2 mL of dichloromethane were successively added under ice-cooling. The reaction mixture was brought to room temperature, and the mixture was stirred over day and night. Moreover, ethyl acetate was added to the mixture, washing by separatory funnel and dehydration-drying were carried out in the same manner as in Example 2(1), and ethyl acetate was removed under reduced pressure to obtain 665 mg of Boc-aminopropyl-ibuprofen (Yield: 91%). The structure was identified by $^1$H-NMR (CDCl$_3$).

$^1$H-NMR (500 MHz, CDCl$_3$) δ (ppm): 0.88 (6H, d, —CH(C$\underline{H}_3$)$_2$), 1.44 (9H, s, Boc), 1.49 (3H, d, —OCOCH(C$\underline{H}_3$)—), 1.75 (2H, m, —NHCH$_2$C$\underline{H}_2$CH$_2$O—), 1.85 (1H, m, —C$\underline{H}_2$CH(CH$_3$)$_2$), 2.45 (2H, d, —C$\underline{H}_2$CH(CH$_3$)$_2$), 3.05 (2H, m, —NHC$\underline{H}_2$CH$_2$CH$_2$O—), 3.69 (1H, q, —OCOC$\underline{H}$(CH$_3$)—), 4.13 (2H, t, —NHCH$_2$CH$_2$C$\underline{H}_2$O—), 4.63 (1H, br, —N$\underline{H}$CH$_2$—), 7.07-7.21 (4H, m, Aromatic H).

In 1 mL of dichloromethane was dissolved 636 mg (1.75 mmol) of the obtained Boc-aminopropyl-ibuprofen, and 4 mL of 4N-Hydrogen chloride in Ethyl acetate was added thereto under ice-cooling. The mixture was stirred under ice-cooling for 10 minutes, thereafter, stirred at room temperature for 3 hours. After disappearance of the Boc-aminopropyl-ibuprofen was confirmed by TLC, diethyl ether was added to the reaction mixture and decantation was carried out 3 times. Then, the mixture was dried under reduced pressure to obtain aminopropyl-ibuprofen (ester) hydrochloride (Yielded amount: 406 mg, Yield: 77%). The structure was identified by $^1$H-NMR (CDCl$_3$).

$^1$H-NMR (500 MHz, CDCl$_3$) δ (ppm): 0.89 (6H, d, —CH(C$\underline{H}_3$)$_2$), 1.47 (3H, d, —OCOCH(C$\underline{H}_3$)—), 1.83 (1H, m, —C$\underline{H}_2$CH(CH$_3$)$_2$), 2.08 (2H, quant, —NHCH$_2$C$\underline{H}_2$CH$_2$O—), 2.44 (2H, d, —C$\underline{H}_2$CH(CH$_3$)$_2$), 3.01 (2H, t, —NHC$\underline{H}_2$CH$_2$CH$_2$O—), 3.71 (1H, q, —OCOC$\underline{H}$(CH$_3$)—), 4.11-4.27 (2H, m, —NHCH$_2$CH$_2$C$\underline{H}_2$O—), 7.06-7.20 (4H, m, Aromatic H), 8.25 (br, H$_3$N$^+$C$\underline{H}_2$—).

(2) Synthesis of Ibuprofen-Introduced Photo-Crosslinked Sodium Hyaluronate Gel (Ibuprofen-Introduced Photo-Cross-Linked HA Gel)

By using 100 mg (0.25 mmol/disaccharide unit) of aminopropyl cinnamate-introduced HA (photo-reactive HA) obtained in Example 1 and 0.1 mL of 0.5 mol/L aminopropyl-ibuprofen (ester) hydrochloride obtained in the above-mentioned (1), 85 mg of ibuprofen-introduced photo-reactive HA was obtained in the same manner as in Example 2(2) as white solid. The degree of substitution of ibuprofen was 9.1%.

A 1% phosphate buffered physiological saline solution of the obtained ibuprofen-introduced photo-reactive HA was prepared, photoirradiation was carried out in the same manner as in Example 2(2) to obtain an ibuprofen-introduced photo-crosslinked HA gel, and further heat treatment at 121° C. for 20 minutes was carried out. When a viscosity thereof was measured by using a rotation viscometer at 20° C., it was 13.1 Pa·s with a standard cone (1°34', 1 rpm).

Example 4

Synthesis of Flurbiprofen-Introduced Photo-Crosslinked Sodium Hyaluronate Gel (1) Synthesis of aminopropyl-flurbiprofen(ester)hydrochloride In 2 mL of dichloromethane were dissolved 352 mg (2 mmol) of Boc-aminopropanol obtained in Preparation example 1 and 489 g (2 mmol) of flurbiprofen, and in the same manner as in Example 3(1), 753 mg of Boc-aminopropyl-flurbiprofen was obtained (Yield: 94%). The structure was identified by $^1$H-NMR (CDCl$_3$).

$^1$H-NMR (500 MHz, CDCl$_3$) δ (ppm): 1.26 (9H, s, Boc), 1.54 (3H, d, —OCOCH(C$\underline{H}_3$)—), 1.80 (2H, quant, —NHCH$_2$C$\underline{H}_2$H$_2$O—), 3.13 (2H, m, —NHC$\underline{H}_2$CH$_2$C$\underline{H}_2$O—), 3.76 (1H, q, —OCOC$\underline{H}$(CH$_3$)—), 4.15 (2H, m, —NHCH$_2$CH$_2$CH$_2$O—), 4.66 (1H, br, —NHCH$_2$—), 7.10-7.55 (9H, m, Aromatic H).

In 1 mL of dichloromethane was dissolved 720 mg (1.79 mmol) of Boc-aminopropyl-flurbiprofen obtained as mentioned above, 4 mL of 4N-Hydrogen chloride in Ethyl acetate was added to the mixture under ice-cooling, and the mixture was stirred under ice-cooling for 3 minutes, thereafter, it was further stirred at room temperature for 3 hours and 10 minutes. After disappearance of Boc-aminopropyl-flurbiprofen was confirmed by TLC, diethyl ether was added to the reaction mixture and decantation was carried out twice. Then, the mixture was dried under reduced pressure to obtain aminopropyl-flurbiprofen (ester) hydrochloride (Yielded amount: 352 mg, Yield: 94%). The structure was identified by $^1$H-NMR (CDCl$_3$).

$^1$H-NMR (500 MHz, CDCl$_3$) δ (ppm): 1.51 (3H, d, —OCOCH(CH$_3$)—) 2.10 (2H, quant, —NHCH$_2$CH$_2$CH$_2$O—), 3.05 (2H, t, —NHCH$_2$CH$_2$CH$_2$O—), 3.76 (1H, q, —OCOCH(CH$_3$)—), 4.13-4.29 (2H, m, —NHCH$_2$CH$_2$CH$_2$O—), 7.07-7.53 (9H, m, Aromatic H), 8.27 (br, H$_3$N$^+$CH$_2$—).

(2) Synthesis of Flurbiprofen-Introduced Photo-Crosslinked Sodium Hyaluronate Gel (Flurbiprofen-Introduced Photo-Crosslinked HA Gel)

In 23 mL of water/23 mL of dioxane was dissolved 200 mg (0.5 mmol/disaccharide unit) of aminopropyl cinnamate-introduced HA (photo-reactive HA) obtained in Example 1, then, 0.2 mL of 1 mol/L HOSu, 0.2 mL of 0.5 mol/L WSCI.HCl, and 0.2 mL of 0.5 mol/L aminopropyl-flurbiprofen (ester) hydrochloride obtained in the above-mentioned (1) were successively added thereto, and the mixture was reacted by stirring over day and night. To the reaction mixture was added 1.5 mL of 5% aqueous sodium hydrogen carbonate solution, and the mixture was stirred for 4 hours. Then, 43 μL of 50% acetic acid was added thereto for neutralization, thereafter 1.2 g of sodium chloride was added to the mixture and the mixture was stirred. To the mixture was added 100 mL of ethanol to cause precipitation, and the precipitate was washed twice with 80% ethanol, twice with ethanol, and once with diethyl ether, and dried under reduced pressure overnight to obtain 204 mg of flurbiprofen-introduced photo-reactive HA. The degree of substitution of flurbiprofen was 9.3%.

A 1% phosphate buffered physiological saline solution of the obtained flurbiprofen-introduced photo-reactive HA was prepared, photoirradiation was carried out in the same manner as in Example 2(2) to obtain a flurbiprofen-introduced photo-crosslinked HA gel, and further heat treatment at 121° C. for 20 minutes was carried out. When a viscosity thereof was measured by using a rotation viscometer at 20° C., it was 21.2 Pa·s with a standard cone (1°34', 1 rpm).

Example 5

Synthesis of Felbinac-Introduced Photo-Cross-Linked Sodium Hyaluronate Gel (1) Synthesis of aminopropyl-felbinac(ester)hydrochloride In 7 ml of dioxane were dissolved 2.04 mmol of Boc-aminopropanol obtained in Preparation example 1, 2.04 mmol of felbinac and 0.41 mmol of DMAP, and then, 2.35 mmol of WSCI.HCl/7 mL of dioxane:dichloromethane (3:4) solution was added thereto under ice-cooling. Further, 3 ml of dimethylformamide (hereinafter also referred to as DMF) was added thereto to make the reaction mixture clear, then, the reaction mixture was brought to room temperature, and stirred over day and night. To the mixture was added ethyl acetate, and washing by separatory funnel were successively carried out with a 5% aqueous citric acid solution, a 5% aqueous sodium hydrogen carbonate solution, and a saturated saline. The mixture was dehydrated and dried over sodium sulfate, and the solvent was distilled off under reduced pressure. The obtained residue was purified by silica gel chromatography (eluent was hexane:ethyl acetate=3:1, containing 0.5% trimethylamine solution) to obtain 623 mg of Boc-aminopropyl-felbinac (Yield: 83%). The structure was identified by $^1$H-NMR (CDCl$_3$).

$^1$H-NMR (500 MHz, CDCl$_3$) δ (ppm): 1.44 (9H, s, Boc), 1.80-1.85 (2H, m, BocHNCH$_2$CH$_2$CH$_2$O—), 3.15-3.19 (2H, m, Boc-HNCH$_2$CH$_2$CH$_2$O—), 3.67 (2H, s, PhCH$_2$—), 4.18 (2H, t, BocHNCH$_2$CH$_2$CH$_2$O—), 4.67 (1H, s, NH), 7.34-7.59 (9H, m, Aromatic).

In 1 mL of dichloromethane was dissolved 1.69 mmol of the obtained Boc-aminopropyl-felbinac, 3 mL of 4N-Hydrogen chloride in Ethyl acetate was added under ice-cooling to the mixture, and the mixture was stirred at room temperature for 2 hours. After disappearance of Boc-aminopropyl-felbinac was confirmed by TLC, diethyl ether was added to the reaction mixture, and the formed precipitate was separated by centrifugation. The obtained precipitate was subjected to decantation with diethyl ether three times, and the mixture was dried under reduced pressure to obtain aminopropyl-felbinac (ester) hydrochloride (Yielded amount: 511.7 mg, Yield: 99%). The structure was identified by $^1$H-NMR (CDCl$_3$).

$^1$H-NMR (500 MHz, CDCl$_3$:CD$_3$OD=1:1) δ (ppm): 1.98-2.04 (2H, m, H$_2$NCH$_2$CH$_2$CH$_2$O—), 2.95 (2H, t, H$_2$NCH$_2$CH$_2$CH$_2$O—), 3.73 (2H, s, -PhCH$_2$—), 4.23 (2H, t, H$_2$NCH$_2$CH$_2$CH$_2$O—), 7.33-7.59 (9H, m, Aromatic).

(2) Synthesis of Felbinac-Introduced Photo-Crosslinked Sodium Hyaluronate Gel (Felbinac-Introduced Photo-Cross-Linked HA Gel)

In 11.5 mL of water/11.5 mL of dioxane was dissolved 100 mg (0.25 mmol/disaccharide unit) of aminopropyl cinnamate-introduced HA (photo-reactive HA) obtained in Example 1, then, 0.1 mL of HOSu (0.1 mmol)/water, 0.1 mL of WSCI.HCl (0.05 mmol)/water, and 2 mL of aminopropyl-felbinac (ester) hydrochloride (0.05 mmol) obtained in the above (1)/water:dioxane (1:1) solution were successively added thereto, and the mixture was reacted by stirring over day and night. To the reaction mixture was added 1.5 mL of 5% aqueous sodium hydrogen carbonate solution, and the mixture was stirred for 4 hours. Then, 43 μL of 50% acetic acid was added to the mixture for neutralization, and thereafter, 600 mg of sodium chloride was added to the same and the mixture was stirred. To the mixture was added 90 mL of ethanol to cause precipitation, it was washed twice with 80% ethanol, twice with ethanol and once with diethyl ether, and dried under reduced pressure at room temperature overnight to obtain 94 mg of felbinac-introduced photo-reactive HA as white solid. The degree of substitution of felbinac was 10.8%.

A 1% phosphate buffered physiological saline solution of the obtained felbinac-introduced photo-reactive HA was prepared, photoirradiation was carried out in the same manner as in Example 2(2) to obtain a felbinac-introduced photo-crosslinked sodium hyaluronate gel, and further heat treatment at 121° C. for 20 minutes was carried out. When a viscosity thereof was measured by using a rotation viscometer at 20° C., it was 7.32 Pa·s with a standard cone (1°34', 1 rpm).

Example 6

Synthesis of Diclofenac-Introduced Photo-Cross-Linked Sodium Hyaluronate Gel

(1) Synthesis of aminopropyl-diclofenac(ester)hydrochloride

In 1 mL of dichloromethane was dissolved 135.8 mg (0.775 mmol) of Boc-aminopropanol obtained in Preparation example 1, then, 229.6 mg (0.775 mmol) of diclofenac which had previously been made an H-form/4 mL of dichloromethane solution, 18.9 mg (0.155 mmol) of DMAP/1 mL of dichloromethane solution and 0.5 mL of DMF were successively added to the mixture, and 191.4 mg (0.998 mmol) of WSCI.HCl/2 mL of dichloromethane solution was added under ice-cooling to the same. The mixture was gradually brought to room temperature and stirred for 7 hours. The reaction mixture was further ice-cooled, 91.9 mg (0.310 mmol) of diclofenac which had previously been made an H-form/1 mL of dichloromethane solution, 7.5 mg (0.061 mmol) of DMAP, and 70.9 mg (0.370 mmol) of WSCI.HCl/1 mL of dichloromethane solution were successively added to the mixture, and then, while the mixture was gradually brought to room temperature the mixture was stirred for 11 hours. The reaction mixture was furthermore ice-cooled, and 91.8 mg (0.310 mmol) of diclofenac which had previously been made an H-form/1 mL of dichloromethane solution and 70.4 mg (0.367 mmol) of WSCI.HCl/1 mL of dichloromethane solution were successively added to the mixture, and then, while the mixture was gradually brought to room temperature, the mixture was stirred for 5 hours. The reaction mixture was still further ice-cooled, and 91.9 mg (0.310 mmol) of diclofenac which had previously been made an H-form/1 mL of dichloromethane solution and 70.7 mg (0.369 mmol) of WSCI.HCl/1 mL of dichloromethane solution were successively added to the mixture, and then, while the mixture was gradually brought to room temperature, the mixture was stirred for 5 hours. The reaction mixture was still further ice-cooled, and 91.7 mg (0.310 mmol) of diclofenac which had previously been made an H-form/1 mL of dichloromethane solution and 71.6 mg (0.374 mmol) of WSCI.HCl/1 mL of dichloromethane solution were successively added to the mixture, and then, while the mixture was gradually brought to room temperature, the mixture was stirred for 14 hours.

Moreover, the reaction mixture was ice-cooled, and 92.0 mg (0.311 mmol) of diclofenac which had previously been made an H-form/1 mL of dichloromethane solution and 72.0 mg (0.376 mmol) of WSCI.HCl/1 mL of dichloromethane solution were successively added to the mixture, and then, while the mixture was gradually brought to room temperature, the mixture was stirred for 6 hours. Ethyl acetate was added to the mixture, the mixture was successively subjected to washing by separatory funnel twice with 5% aqueous citric acid solution, twice with 5% aqueous sodium bicarbonate solution and saturated saline solution. After dehydration with sodium sulfate, ethyl acetate was distilled off under reduced pressure. The residue was purified by silica gel column chromatography (Eluent was hexane:ethyl acetate (7:1) containing 0.5% triethylamine solution) to obtain 280.2 mg of the title compound (80%). The structure was identified by $^1$H-NMR.

$^1$H-NMR (500 MHz, CDCl$_3$) δ (ppm): 1.44 (9H, s, Boc), 1.85 (2H, quant, —NHCH$_2$CH$_2$CH$_2$O—), 3.16 (2H, q, —NHCH$_2$CH$_2$CH$_2$O—), 3.82 (2H, s, Ph-CH$_2$—CO), 4.22 (2H, t, —NHCH$_2$CH$_2$CH$_2$O—), 4.68 (1H, s, NH), 6.54-7.35 (8H, m, Aromatic H, NH).

In 2 mL of dichloromethane was dissolved 1019 mg of the obtained Boc-aminopropyl-dichlofenac, and 8 mL of 4N-Hydrogen chloride in Ethyl acetate was added to the mixture under ice-cooling and the mixture was stirred for 3 hours. To the mixture was added 150 mL of diethyl ether to form a precipitate, and the precipitate was dried under reduced pressure to obtain 791 mg of aminopropyl-dichlofenac (ester) hydrochloride (90%). The structure was identified by $^1$H-NMR.

$^1$H-NMR (500 MHz, CDCl$_3$) δ (ppm): 2.13 (2H, quant, —NHCH$_2$CH$_2$CH$_2$O—), 3.08 (2H, t, —NHCH$_2$CH$_2$CH$_2$O—), 3.84 (2H, s, Ph-CH$_2$—CO), 4.25 (2H, t, —NHCH$_2$CH$_2$CH$_2$O—), 6.52-7.33 (8H, m, Aromatic H, NH).

(2) Synthesis of Dichlofenac-Introduced Photo-Crosslinked Sodium Hyaluronate Gel (Dichlofenac-Introduced Photo-Crosslinked HA Gel)

In 12.7 mL of water/12.7 mL of dioxane was dissolved 110 mg (0.28 mmol/disaccharide unit) of aminopropyl cinnamate-introduced HA (photo-reactive HA) obtained in Example 1, 0.11 mL of HOSu (0.11 mmol)/water, 0.11 mL of WSCI.HCl (0.055 mmol)/water and 2 mL of aminopropyl-dichlofenac (ester) hydrochloride (0.055 mmol) obtained in Example 6(1)/water:dioxane (1:1) solution were successively added to the mixture, and the mixture was reacted by stirring over day and night. To the mixture was added 1.65 mL of a 5% aqueous sodium hydrogen carbonate solution, and the mixture was stirred for 4 hours. To the mixture was added 47 µL of 50% acetic acid for neutralization, 660 mg of sodium chloride was added thereto and the mixture was stirred. To the mixture was added 90 ml of ethanol to cause precipitation, then the precipitate was washed twice with 80% ethanol, twice with ethanol and then with diethyl ether, and dried at room temperature under reduced pressure overnight. 111 mg of dichlofenac-introduced photo-reactive HA was obtained as white solid. The degree of substitution of the dichlofenac measured by $^1$H-NMR was 13.6%.

A 1% phosphate buffered physiological saline solution of the obtained dichlofenac-introduced photo-reactive HA mentioned above was prepared, photoirradiation was carried out in the same manner as in Example 2(2) to obtain a dichlofenac-introduced photo-crosslinked sodium hyaluronate gel.

Example 7

Synthesis of Etodolac-Introduced Photo-Cross-Linked Sodium Hyaluronate Gel

(1) Synthesis of aminopropyl-etodolac(ester)hydrochloride

In 4 mL of dichloromethane were dissolved 178.8 mg (1.02 mmol) of Boc-aminopropanol obtained in Preparation example 1, 293.8 mg (1.02 mmol) of etodolac and 23.8 mg (0.20 mmol) of DMAP, and 233.8 mg (1.22 mmol) of WSCI.HCl/2 mL of dichloromethane solution was added thereto under ice-cooling, then while the mixture was gradually brought to room temperature, the mixture was stirred over day and night. Moreover, under ice-cooling, 68.8 mg (0.36 mmol) of WSCI.HCl/2 mL of dichloromethane solution was added to the mixture, and then, while the mixture was gradually brought to room temperature, the mixture was stirred for 80 minutes. Ethyl acetate was added to the mixture, and the mixture was successively subjected to washing by separatory funnel twice with 5% aqueous citric acid solution, twice with 5% aqueous sodium bicarbonate solution and then saturated saline. After dehydration with sodium sulfate, ethyl acetate was distilled off under reduced pressure. The residue was purified by silica gel column chromatography (Eluent was hexane:ethyl acetate (3:1) containing 0.5% triethylamine solution) to obtain 436.3 mg of Boc-aminopropyl-etodolac (Yield: 96%). The structure was identified by $^1$H-NMR (CDCl$_3$).

$^1$H-NMR (500 MHz, CDCl$_3$) δ (ppm): 0.83 (3H, t, —CH$_2$CH$_3$), 1.37 (3H, t, —CH$_2$CH$_3$), 1.43 (9H, s, Boc), 1.79 (2H, quant, —NHCH$_2$CH$_2$CH$_2$O—), 3.14 (2H, q, —NHCH$_2$CH$_2$CH$_2$O—), 4.10-4.22 (2H, m, —NHCH$_2$CH$_2$CH$_2$O—), 4.63 (1H, s, NH), 7.00-7.37 (3H, m, Aromatic H), 8.97 (1H, s, NH).

In 1 mL of dichloromethane was dissolved 421.5 mg (0.948 mmol) of Boc-aminopropyl-etodolac obtained as mentioned above, 3 mL of 4N-Hydrogen chloride in Ethyl acetate was added thereto under ice-cooling and the mixture was stirred for 3 hours. To the mixture were added diethyl ether and hexane to cause precipitation, and the precipitate was dried under reduced pressure. The precipitate was purified by silica gel column chromatography (Eluent was chloroform:methanol (3:1) containing 0.5% triethylamine solution) to obtain 197.6 mg of aminopropyl-etodolac (ester) hydrochloride (55%). The structure was identified by $^1$H-NMR (CDCl$_3$).

$^1$H-NMR (500 MHz, CDCl$_3$) δ (ppm): 0.81 (3H, t, —CH$_2$CH$_3$), 1.35 (3H, t, —CH$_2$CH$_3$), 1.92-2.17 (4H, m, —CH$_2$CH$_3$, —NHCH$_2$CH$_2$CH$_2$O—), 4.12 (1H, quant, —NHCH$_2$CH$_2$CH$_2$O—), 4.20 (1H, quant, —NHCH$_2$CH$_2$CH$_2$O—), 6.99-7.35 (3H, m, Aromatic H), 8.99 (1H, s, NH).

(2) Synthesis of Etodolac-Introduced Photo-Crosslinked Sodium Hyaluronate Gel (Etodolac-Introduced Photo-Cross-Linked HA Gel)

In 10.3 mL of water/10.3 mL of dioxane was dissolved 89.2 mg (0.223 mmol/disaccharide unit) of aminopropyl cinnamate-introduced HA obtained in Example 1, then, to the mixture were successively added 0.1 mL of HOSu (0.0892 mmol)/water, 0.1 mL of WSCI.HCl (0.0446 mmol)/water and 2 mL of aminopropyl-etodolac (ester) hydrochloride (0.0446 mmol) obtained in Example 7(1)/water:dioxane (1:1) solution, and the mixture was reacted by stirring over day and night. To the reaction mixture was added 1.34 mL of a 5% aqueous sodium hydrogen carbonate solution, and the mixture was stirred for 4 hours. To the reaction mixture was added 38 μL of 50% acetic acid to neutralize the mixture, then, 540 mg of sodium chloride was added thereto and the mixture was stirred. 90 ml of ethanol was added to the mixture to cause precipitation, the precipitate was washed twice with 80% ethanol, twice with ethanol and then with diethyl ether, and dried at room temperature under reduced pressure overnight. 80 mg of etodolac-introduced photo-reactive HA (white solid) was obtained. The degree of substitution of etodolac measured by HPLC was 7.7%.

A 1% phosphate buffered physiological saline solution of the obtained etodolac-introduced photo-reactive HA as mentioned above was prepared, photoirradiation was carried out in the same manner as in Example 2(2) to obtain an etodolac-introduced photo-crosslinked HA gel, and further heat treatment at 121° C. for 20 minutes was carried out. When a viscosity thereof was measured by using a rotation viscometer at 20° C., it was 12.7 Pa·s with a standard cone (1°34', 1 rpm).

Example 8

Synthesis of Actarit-Introduced Photo-Cross-Linked Sodium Hyaluronate Gel

(1) Synthesis of aminopropyl-actarit(ester)hydrochloride (Disease-Modifying Anti-Rheumatic Drugs)

In 2 mL of dichloromethane was dissolved 123.1 mg (0.703 mmol) of Boc-aminopropanol obtained in Preparation example 1, 136.0 mg (0.704 mmol) of actarit/1 mL of DMF solution was added thereto, and 17.1 mg (0.140 mmol) of DMAP and 175.4 mg (0.915 mmol) of WSCI.HCl were successively added thereto under ice-cooling, and then, while the mixture was gradually brought to room temperature, the mixture was reacted by stirring over day and night. To the reaction mixture was added ethyl acetate, the mixture was subjected to washing by separatory funnel and dried by dehydration in the same manner as in Example 5(1), then, the solvent was distilled off and the residue was purified by silica gel column chromatography. As the eluent for silica gel chromatography, hexane:ethyl acetate (1:2) containing 0.5% triethylamine solution was used. 203.1 mg (83%) of aminopropyl-actarit (ester) hydrochloride was obtained. The structure was identified by $^1$H-NMR (CDCl$_3$).

$^1$H-NMR (500 MHz, CDCl$_3$) δ (ppm): 1.44 (9H, s, Boc), 1.80 (2H, quant, —NHCH$_2$CH$_2$CH$_2$O—), 2.18 (3H, s, NAc), 3.14 (2H, q, —NHCH$_2$CH$_2$CH$_2$O—), 3.59 (2H, s, Ph-CH$_2$—CO), 4.15 (2H, t, —NHCH$_2$CH$_2$CH$_2$O—), 4.66 (1H, s, NH), 7.13 (1H, s, NH), 7.23 (2H, d, Aromatic H), 7.46 (2H, d, Aromatic H).

In 2 mL of dichloromethane was dissolved 201.3 mg (0.574 mmol) of the obtained Boc-aminopropyl-actarit, 3 mL of 4N-Hydrogen chloride in Ethyl acetate was added thereto under ice-cooling and the mixture was stirred for 3 hours. Diethyl ether was added to the mixture to cause precipitation, the precipitate was washed twice with diethyl ether, and then, dried under reduced pressure to obtain 161.3 mg of aminopropyl-actarit (ester) hydrochloride (98%). The structure was identified by $^1$H-NMR (CDCl$_3$).

$^1$H-NMR (500 MHz, CD$_3$OD) δ (ppm): 1.94-1.99 (2H, m, —NHCH$_2$CH$_2$CH$_2$O—), 2.11 (3H, s, NAc), 2.94 (2H, t, —NHCH$_2$CH$_2$CH$_2$O—), 3.63 (2H, s, Ph-CH$_2$—CO), 4.19 (2H, t, —NHCH$_2$CH$_2$CH$_2$O—), 7.22-7.51 (4H, m, Aromatic H).

(2) Synthesis of Actarit-Introduced Photo-Crosslinked Sodium Hyaluronate Gel (Actarit-Introduced Photo-Cross-Linked HA Gel)

In 11.5 mL of water/11.5 mL of dioxane was dissolved 100 mg (0.25 mmol/disaccharide unit) of aminopropyl cinnamate-introduced HA (photo-reactive HA) obtained in Example 1, then, 0.1 mL of HOSu (0.2 mmol)/water, 0.1 mL of WSCI.HCl (0.1 mmol)/water, and 2 mL of aminopropyl-actarit (ester) hydrochloride (0.1 mmol) obtained in the above-mentioned (1)/water:dioxane (1:1) solution were successively added thereto, and the mixture was reacted by stirring over day and night. To the reaction mixture was added 1.5 mL of a 5% aqueous sodium hydrogen carbonate solution, and the mixture was stirred for 5 hours and 10 minutes. The reaction mixture was neutralized in the same manner as in Example 5(2), then, the product was precipitated with ethanol, and the precipitate was washed and dried under reduced pressure to obtain 100 mg of actarit-introduced photo-reactive HA as white solid. The degree of substitution of actarit measured by HPLC was 15.6%.

A 1 phosphate buffered physiological saline solution of the obtained actarit-introduced photo-reactive HA was prepared, photoirradiation was carried out in the same manner as in Example 2(2) to obtain an actarit-introduced photo-crosslinked HA gel, and further heat treatment at 121° C. for 20 minutes was carried out. When a viscosity thereof was measured by using a rotation viscometer at 20° C., it was 10.8 Pa·s with a standard cone (1034', 1 rpm).

Example 9

Synthesis of Felbinac-Introduced Photo-Cross-Linked HA Gel in which Aminopropyl Cinnamate Hydrochloride and Aminopropyl-Felbinac(ester)hydrochloride are Simultaneously Added In 11.25 mL of water/11.25 mL of dioxane was dissolved 100 mg (0.25 mmol/disaccharide unit) of hyaluronic acid having a weight average molecular weight of 800,000, 0.1 mL of HOSu (0.275 mmol)/water and 0.1 mL of WSCI.HCl (0.1375 mmol)/water were added to the mixture, and further, aminopropyl-felbinac (ester) hydrochloride (0.05 mmol) obtained in Example 5(1) and 2 mL of aminopropyl cinnamate hydrochloride (0.0875 mmol) obtained in Preparation example 2/water:dioxane (1:1) solution were simultaneously added to the mixture, and the mixture was reacted by stirring over day and night. In the same manner as in Example 5(2), to the reaction mixture was added 1.5 mL of a 5% aqueous sodium hydrogen carbonate solution, and the mixture was stirred for 4 hours. Then, the reaction mixture was neutralized, precipitate was formed by adding ethanol, and the precipitate was washed and dried under reduced pressure to obtain 92 mg of felbinac-introduced photo-reactive HA as white solid. The degree of substitution of felbinac measured by HPLC was 8.7%, and the degree of substitution of trans-cinnamic acid was 13.3%.

A 1% phosphate buffered physiological saline solution of the obtained felbinac-introduced photo-reactive HA was prepared, photoirradiation was carried out in the same manner as in Example 2(2) to obtain a felbinac-introduced photo-crosslinked HA gel, then, heat treatment was carried out. When a viscosity thereof was measured by using a rotation viscometer at 20° C., it was 12.1 Pa·s with a standard cone (1°34', 1 rpm).

From the above-mentioned results, it can be clarified that even when aminopropyl cinnamate hydrochloride and aminopropyl-felbinac (ester) hydrochloride are simultaneously introduced, the produced drug-containing photoreactive hyaluronic acid can be gelled.

Example 10

Synthesis of Felbinac-Introduced Photo-Cross-Linked HA Gel by Adding Aminopropyl Cinnamate Hydrochloride to Aminopropyl-Felbinac-Introduced Sodium Hyaluronate (1) Felbinac-Introduced Sodium Hyaluronate (Felbinac-Introduced HA)

In 56.3 mL of water/56.3 mL of dioxane was dissolved 500 mg (1.25 mmol/disaccharide unit) of hyaluronic acid having a weight average molecular weight of 800,000, and to the mixture were successively added 0.5 mL of HOSu (0.5 mmol)/water, 0.5 mL of WSCI.HCl (0.25 mmol)/water, and 5 mL of aminopropyl-felbinac (ester) hydrochloride (0.25 mmol) obtained in Example 5(1)/water:dioxane (1:1) solution, and the mixture was reacted by stirring over day and night. To the reaction mixture was added 7.5 mL of a 5% aqueous sodium hydrogen carbonate solution, and the mixture was stirred for 4 hours. To the reaction mixture was added 215 μL of 50% acetic acid to neutralize the mixture, then, 3 g of sodium chloride was added thereto and the mixture was stirred. 500 ml of ethanol was added to the mixture to cause precipitation, and the precipitate was successively washed twice with 80% ethanol, twice with ethanol and then with diethyl ether and dried at room temperature under reduced pressure overnight. 489 mg of felbinac-introduced HA was obtained as white solid. The degree of substitution of felbinac measured by HPLC was 7.6%.

(2) Felbinac-Introduced Photo-Crosslinked HA Gel

In 11.25 mL of water/11.25 mL of dioxane was dissolved 100 mg (0.25 mmol/disaccharide unit) of felbinac-introduced HA obtained in Example 10(1), then, to the mixture were successively added 0.2 mL of HOSu (0.2 mmol)/water, 0.2 mL of WSCI.HCl (0.1 mmol)/water, and 2 mL of aminopropyl cinnamate hydrochloride (0.1 mmol) produced in Example 2/water:dioxane (1:1) solution, and the mixture was reacted by stirring over day and night. To the reaction mixture was added 1.5 mL of a 5% aqueous sodium hydrogen carbonate solution, and the mixture was stirred for 4 hours. Then, in the same manner as in Example 5(2), the reaction mixture was neutralized, precipitate was formed by adding ethanol, and the precipitate was washed and dried under reduced pressure to obtain 85 mg of felbinac-introduced photo-reactive HA as white solid. The degree of substitution of trans-cinnamic acid measured by HPLC was 14.8%.

A 1% phosphate buffered physiological saline solution of the obtained felbinac-introduced photo-reactive HA was prepared, photoirradiation was carried out in the same manner as in Example 2(2) to obtain a felbinac-introduced photo-crosslinked HA gel, and thereafter heat treatment at 121° C. for 20 minutes was carried out. When a viscosity thereof was measured by using a rotation viscometer at 20° C., it was 27.08 Pa·s with a standard cone (1034', 1 rpm).

Example 11

Synthesis of Felbinac-Introduced Photo-Cross-Linked HA Gel by Stepwise Addition of Aminopropyl-felbinac(ester)hydrochloride and Aminopropyl Cinnamate Hydrochloride In 11.25 mL of water/11.25 mL of dioxane was dissolved 100 mg (0.25 mmol/disaccharide unit) of hyaluronic acid having a weight average molecular weight of 800,000, then, to the mixture were successively added 0.1 mL of HOSu (0.1 mmol)/water, 0.1 mL of WSCI.HCl (0.05 mmol)/water, and 2 mL of aminopropyl-felbinac (ester) hydrochloride (0.05 mmol) obtained in Example 5(1)/water:dioxane (1:1) solution, and the mixture was stirred for 6 hours. Moreover, to the mixture were successively added 0.2 mL of HOSu (0.2 mmol)/water, 0.2 mL of WSCI.HCl (0.1 mmol)/water, and 2 mL of aminopropyl cinnamate hydrochloride (0.1 mmol)/water:dioxane (1:1) solution, and the mixture was reacted by stirring over day and night. To the reaction mixture was added 1.5 mL of a 5% aqueous sodium hydrogen carbonate solution, and the mixture was stirred for 5 hours and 30 minutes. To the reaction mixture was added 43 µL of 50% acetic acid to neutralize the mixture, 0.6 g of sodium chloride was added thereto and the mixture was stirred. 100 ml of ethanol was added to the mixture to cause precipitation, and the precipitate was successively washed twice with 80% ethanol, twice with ethanol and then with diethyl ether, and dried at room temperature under reduced pressure overnight. 90 mg of felbinac-introduced photo-reactive HA was obtained as white solid. The degree of substitution of felbinac and trans-cinnamic acid measured by HPLC were 11.4 and 13.9%, respectively.

A 1% phosphate buffered physiological saline solution of the obtained felbinac-introduced photo-reactive HA was prepared, photoirradiation was carried out in the same manner as in Example 2(2) to obtain a felbinac-introduced photo-crosslinked HA gel, and thereafter heat treatment at 121° C. for 20 minutes was carried out. When a viscosity thereof was measured by using a rotation viscometer at 20° C., it was 12.95 Pa·s with a standard cone (1°34', 1 rpm).

Example 12

Synthesis of Felbinac-Introduced Photo-Cross-Linked HA Gel by Stepwise Addition of Aminopropyl Cinnamate Hydrochloride and Aminopropyl-felbinac(ester)hydrochloride In 11.25 mL of water/11.25 mL of dioxane was dissolved 100 mg (0.25 mmol/disaccharide unit) of hyaluronic acid having a weight average molecular weight 800,000, then, to the mixture were successively added 0.2 mL of HOSu (0.2 mmol)/water, 0.2 mL of WSCI.HCl (0.1 mmol)/water, and 2 mL of aminopropyl cinnamate hydrochloride (0.1 mmol)/water:dioxane (1:1) solution, and the mixture was stirred for 6 hours. Moreover, to the mixture were successively added 0.1 mL of HOSu (0.1 mmol)/water, 0.1 mL of WSCI.HCl (0.05 mmol)/water, and 2 mL of aminopropyl-felbinac (ester) hydrochloride (0.05 mmol) obtained in Example 5(1)/water:dioxane (1:1) solution, and the mixture was reacted by stirring over day and night. In the same manner as in Example 11, to the reaction mixture was added 1.5 mL of a 5% aqueous sodium hydrogen carbonate solution and the mixture was stirred for 5 hours and 30 minutes, the reaction mixture was neutralized, precipitate was formed by adding ethanol, and the precipitate was washed and dried under reduced pressure. 89 mg of felbinac-introduced photo-reactive HA was obtained as white solid. The degree of substitution of trans-cinnamic acid and felbinac measured by HPLC were 18.2 and 5.7%, respectively.

A 1% phosphate buffered physiological saline solution of the obtained felbinac-introduced photo-reactive HA was prepared, photoirradiation was carried out in the same manner as in Example 2(2) to obtain a felbinac-introduced photo-crosslinked HA gel, and thereafter, heat treatment at 121° C. for 20 minutes was carried out. When a viscosity thereof was measured by using a rotation viscometer at 20° C., it was 22.58 Pa·s with a standard cone (1°34', 1 rpm).

Example 13

Viscosity, characteristics and extrusion feeling from an injection needle of 23 G of 7 kinds in total of the drug-containing cross-linked HA gels of the above-mentioned Examples 2 to 5 and Examples 7 to 9 were examined. Evaluation was carried out in accordance with the following criteria.

[Characteristics]

Extrusion state from a tip of injection needle: In the test of the below mentioned "extrusion feeling", with regard to substances to be tested which are capable of extruding, that formed a mass or a lump having a shape-maintaining property at the tip of the injection needle when it was slowly extruded from an injection needle with 23 G to down-ward with an angle of about 450 was evaluated to as (○), and that which did not form a mass was evaluated to as (X).

[Extrusion Feeling]

○: easily extruded
X: difficulty extruded

Incidentally, with regard to the criteria for the extrusion feeling, within the range of a limit pressure (0.5 to 5 kg/cm²), when a whole gel (2 ml to 5 ml) filled in a syringe having a volume of 5 ml was extruded through an injection needle of 23 gauge, it was evaluated to as easily extruded (○). Also, according to the same operation, when not a whole gel filled in a syringe was extruded, for example, by clogging due to insoluble materials, it was evaluated to as difficulty extruded (X).

The results are shown in the following Table.

TABLE 1

| Example | Introduced drug | Degree of substitution of cinnamic acid (%) | Degree of substitution of drug (%) | Viscosity | Extruded state | Extrusion feeling |
|---|---|---|---|---|---|---|
| 2 | Naproxen | 16.2 | 9.3 | 34.7 | ○ | ○ |
| 3 | Ibuprofen | 16.2 | 9.1 | 13.1 | ○ | ○ |
| 4 | Flubiprofen | 16.2 | 9.3 | 21.2 | ○ | ○ |
| 5 | Felbinac | 16.2 | 10.8 | 7.32 | X | ○ |
| 7 | Etodolac | 16.2 | 7.7 | 12.7 | ○ | ○ |
| 8 | Actarit | 16.2 | 15.6 | 10.8 | ○ | ○ |
| 9 | Felbinac | 13.3 | 8.7 | 12.1 | Δ | ○ |

The invention claimed is:

1. A drug-introduced photo-reactive hyaluronic acid derivative which comprises a photo-reactive group and a drug both being bound to hyaluronic acid through covalent bonds via a first and second spacer, respectively, wherein the photo-reactive group is a cinnamic acid, the drug is a non-steroidal anti-inflammatory drug or an anti-rheumatic drug, each of the first and second spacers are a residue of an amino alcohol, the photo-reactive group and the drug are each bonded to one of the first and second spacers through an ester bond and each of said first and second spacers bonded to the photo-reactive group and the drug is bonded to a carboxyl group of the hyaluronic acid through an amide bond and the drug-introduced photo-reactive hyaluronic acid derivative is soluble in an aqueous medium.

2. The drug-introduced photo-reactive hyaluronic acid derivative according to claim 1, wherein degree of substitutions of the photo-reactive group and the drug in total are 10 to 45 mol % per a molar number of a repeating disaccharide unit of the hyaluronic acid.

3. The drug-introduced photo-reactive hyaluronic acid derivative according to claim 1, which is obtainable by subjecting the drug-introduced photoreactive hyaluronic acid to an alkali treatment before photo-crosslinking in preparation steps.

4. A drug-introduced photo-crosslinked hyaluronic acid derived gel which comprises a photo-crosslinked hyaluronic acid derived gel in which a drug is introduced therein by a covalent bond via a second spacer, wherein the photo-reactive group is a cinnamic acid, the drug is a non-steroidal anti-inflammatory drug or an anti-rheumatic drug, a first spacer and the second spacer are each a residue of an amino alcohol, the photo-reactive group is bonded to the first spacer through an ester bond and the drug is bonded to the second spacer through an ester bond, the second spacer bonded to the drug is bonded to a carboxyl group of the hyaluronic acid through an amide bond and the first spacer bonded to the photo-reactive group is bonded to a carboxyl group of the hyaluronic acid through an amide bond, the photo-reactive group has a cross-linking structure forming a cyclobutane ring, and the gel is in a state of being capable of extruding from an injection device.

5. The drug-introduced photo-crosslinked hyaluronic acid derived gel according to claim 4, wherein the gel is obtainable by irradiating an aqueous solution of a drug-introduced photo-reactive hyaluronic acid derivative with ultraviolet rays.

6. The drug-introduced photo-crosslinked hyaluronic acid derived gel according to claim 4, wherein it is capable of extruding from an injection device mounted with an injection needle of 20 to 25 gauge and a pressure of 0.5 to 5 kg/cm$^2$.

7. A medicament comprising the drug-introduced photo-crosslinked hyaluronic acid derived gel according to claim 4.

8. The medicament according to claim 7, wherein it is used for a drug-sustained release preparation having a property of gradually releasing a drug introduced into hyaluronic acid which comprises the drug-introduced photo-crosslinked hyaluronic acid derived gel.

9. The medicament according to claim 7, wherein it is used for a preparation for local administration.

10. A drug-filled injection device which comprises the drug-introduced photo-crosslinked hyaluronic acid derived gel according to claim 4 being filled in an injection device which is sealed by a gasket.

11. A kit comprises the drug-filled injection device according to claim 10.

12. A method for treating osteoarthritis which comprises administering an effective amount of the medicament according to claim 7 to a diseased area.

13. A process for preparing a drug-introduced photo-crosslinked hyaluronic acid derived gel capable of injecting, which comprises the steps of preparing a solution by dissolving the drug-introduced photo-reactive hyaluronic acid derivative according to claim 1 in an aqueous solution, and irradiating to the solution with ultraviolet rays.

14. The process for preparing a drug-introduced photo-crosslinked hyaluronic acid derived gel capable of injecting according to claim 13, which comprises sterilizing the aqueous solution after irradiation with ultraviolet rays.

15. The drug-introduced photo-reactive hyaluronic acid derivation according to claim 1, wherein the drug is at least one selected from the group consisting of naproxen, ibuprofen, flurbiprofen, felbinac, diclofenac, etodolac and actarit.

16. The drug-introduced photo-cross-linked hyaluronic acid derived gel according to claim 4, wherein the drug is at least one selected from the group consisting of naproxen, ibuprofen, flurbiprofen, felbinac, diclofenac, etololac and actarit.

17. The drug-introduced photo-crosslinked hyaluronic derived gel according to claim 4 wherein the degree of substitutions of the photo-reactive group and the drug in total are 10 to 45 mol % per a molar number of a repeating disaccharide unit of the hyaluronic acid.

18. The drug-introduced photo-crosslinked hyaluronic acid derived gel according to claim 16, wherein degree of substitutions of the photo-reactive group and the drug in total are 10 to 45 mol % per a molar number of a repeating disaccharide unit of the hyaluronic acid.

19. The drug-introduced photo-crosslinked hyaluronic acid derived gel according to claim 16, wherein the gel is obtainable by irradiating an aqueous solution of a drug-introduced photo-reactive hyaluronic acid derivative with ultraviolet rays.

20. The drug-introduced photo-crosslinked acid derived gel according to claim 17, wherein the gel is obtainable by irradiating to an aqueous solution of a drug-introduced photo-reactive hyaluronic acid derivative with ultraviolet rays.

21. The drug-introduced photo-crosslinked acid derived gel according to claim 18, wherein the gel is obtainable by irradiating an aqueous solution of a drug-introduced photo-reactive hyaluronic acid derivative with ultraviolet rays.

22. The drug-introduced photo-crosslinked acid derived gel according to claim 4, which is obtainable by subjecting the drug-introduced photoreactive hyaluronic acid to an alkali treatment before photo-crosslinking in preparation steps.

23. The drug-introduced photo-crosslinked acid derived gel according to claim 5, which is obtainable by subjecting the drug-introduced photoreactive hyaluronic acid to an alkali treatment before photo-crosslinking in preparation steps.

24. The drug-introduced photo-crosslinked acid derived gel according to claim 4, wherein the spacer bound to the photo-reactive group is bonded to carboxyl groups of the hyaluronic acid.

* * * * *

UNITED STATES PATENT AND TRADEMARK OFFICE
CERTIFICATE OF CORRECTION

PATENT NO. : 8,354,392 B2
APPLICATION NO. : 11/994981
DATED : January 15, 2013
INVENTOR(S) : Miyamoto et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 707 days.

Signed and Sealed this
First Day of September, 2015

Michelle K. Lee
*Director of the United States Patent and Trademark Office*